(12) United States Patent
Heneveld et al.

(10) Patent No.: US 8,343,132 B2
(45) Date of Patent: Jan. 1, 2013

(54) APPARATUS AND METHODS FOR INJECTING HIGH VISCOSITY DERMAL FILLERS

(75) Inventors: Scott Heneveld, Whitmore, CA (US); John R. Krumme, Woodside, CA (US); Stacy R. Smith, Del Mar, CA (US); Christian Walton, Belmont, CA (US)

(73) Assignee: Nordson Corporation, Westlake, OH (US)

( * ) Notice: Subject to any disclaimer, the term of this patent is extended or adjusted under 35 U.S.C. 154(b) by 140 days.

(21) Appl. No.: 12/871,405

(22) Filed: Aug. 30, 2010

(65) Prior Publication Data

US 2010/0324531 A1 Dec. 23, 2010

Related U.S. Application Data

(63) Continuation of application No. 12/114,194, filed on May 2, 2008, now abandoned, which is a continuation-in-part of application No. PCT/US2007/023226, filed on Nov. 1, 2007.

(60) Provisional application No. 60/856,430, filed on Nov. 3, 2006, provisional application No. 60/857,546, filed on Nov. 8, 2006, provisional application No. 60/857,755, filed on Nov. 8, 2006, provisional application No. 60/964,066, filed on Aug. 8, 2007, provisional application No. 60/993,541, filed on Sep. 12, 74, provisional application No. 61/016,223, filed on Dec. 21, 2007.

(51) Int. Cl.
*A61M 31/00* (2006.01)

(52) U.S. Cl. ......... 604/506; 604/500; 604/507; 604/511

(58) Field of Classification Search .................. 604/118, 604/121, 131, 140–143, 146, 147, 150–152, 604/163.03, 164.02, 167.01, 232, 234, 236, 604/246, 248, 249, 500, 506, 507, 511; 600/431, 600/432

See application file for complete search history.

(56) References Cited

U.S. PATENT DOCUMENTS

| | | | |
|---|---|---|---|
| 2,390,246 A | 12/1945 | Folkman |
| 2,469,642 A | 5/1949 | Grewe |
| 2,605,763 A | 8/1952 | Smoot |
| 2,670,241 A | 2/1954 | Pyles |
| 3,258,176 A | 6/1966 | Raczynski |
| 3,827,604 A | 8/1974 | Hamilton et al. |

(Continued)

FOREIGN PATENT DOCUMENTS

JP 2002322448 A 11/2002

(Continued)

OTHER PUBLICATIONS

Acist Medical Systems, Inc.; Empower MR, Contrast Injection System, Brochure, 2009.

(Continued)

*Primary Examiner* — Bhisma Mehta
*Assistant Examiner* — Larry R Wilson
(74) *Attorney, Agent, or Firm* — Wood, Herron & Evans, L.L.P.

(57) ABSTRACT

A method includes inserting a distal end portion of a needle of a medical injector into a skin of a body. An energy source operatively coupled to the medical injector is actuated such that a dermal filler is conveyed from the medical injector into the skin through the distal end portion of the needle. The distal end portion of the needle is moved within the skin during the actuating.

33 Claims, 10 Drawing Sheets

U.S. PATENT DOCUMENTS

| | | | |
|---|---|---|---|
| 4,260,130 A | 4/1981 | Brehm | |
| 4,332,246 A | 6/1982 | Thomson | |
| 4,351,335 A | 9/1982 | Whitney et al. | |
| 4,634,027 A | 1/1987 | Kanarvogel | |
| 4,636,198 A | 1/1987 | Stade | |
| 4,667,084 A | 5/1987 | Regge | |
| 4,705,509 A | 11/1987 | Stade | |
| 4,735,619 A | 4/1988 | Sperry et al. | |
| 4,790,824 A | 12/1988 | Morrow et al. | |
| 4,861,340 A | 8/1989 | Smith et al. | |
| 4,932,592 A | 6/1990 | Abbott et al. | |
| 4,944,726 A | 7/1990 | Hilal et al. | |
| 4,993,948 A | 2/1991 | Cameron et al. | |
| 5,019,037 A | 5/1991 | Wang et al. | |
| 5,066,276 A | 11/1991 | Wang | |
| 5,074,443 A | 12/1991 | Fujii et al. | |
| 5,204,382 A | 4/1993 | Wallace et al. | |
| 5,366,498 A | 11/1994 | Brannan et al. | |
| 5,370,630 A | 12/1994 | Smidebush et al. | |
| 5,375,738 A | 12/1994 | Walsh et al. | |
| 5,383,605 A | 1/1995 | Teague | |
| 5,383,851 A | 1/1995 | McKinnon, Jr. et al. | |
| 5,383,930 A | 1/1995 | Brannan et al. | |
| 5,535,919 A | 7/1996 | Ganzer et al. | |
| 5,540,657 A | 7/1996 | Kurjan et al. | |
| 5,637,095 A | 6/1997 | Nason et al. | |
| 5,782,633 A | 7/1998 | Muhlbauer | |
| 5,826,584 A | 10/1998 | Schmitt | |
| 5,830,194 A | 11/1998 | Anwar et al. | |
| 5,833,661 A | 11/1998 | Trapp et al. | |
| 6,146,361 A | 11/2000 | DiBiasi et al. | |
| 6,152,386 A | 11/2000 | Bullock et al. | |
| 6,210,359 B1 | 4/2001 | Patel et al. | |
| 6,379,152 B1 | 4/2002 | Dragan | |
| 6,550,480 B2 | 4/2003 | Feldman et al. | |
| 6,616,627 B2 | 9/2003 | Willis et al. | |
| 6,623,455 B2 | 9/2003 | Small et al. | |
| 6,644,625 B1 | 11/2003 | Jacobs et al. | |
| 6,736,792 B1 | 5/2004 | Liu | |
| 6,767,310 B2 | 7/2004 | Amanuma et al. | |
| 6,780,170 B2 | 8/2004 | Fago et al. | |
| 6,926,699 B2 | 8/2005 | Stone | |
| 6,929,623 B2 | 8/2005 | Stone | |
| 6,938,795 B2 | 9/2005 | Barton, Jr. et al. | |
| 6,957,747 B2 | 10/2005 | Peeler et al. | |
| 6,997,904 B2 | 2/2006 | Sculati | |
| 7,018,365 B2 | 3/2006 | Strauss et al. | |
| 7,041,084 B2 | 5/2006 | Fojtik | |
| 7,195,610 B1 | 3/2007 | Flachbart | |
| 7,270,648 B2 | 9/2007 | Kazemzadeh | |
| 7,637,900 B2 | 12/2009 | Burgess | |
| 2001/0018484 A1 | 8/2001 | Bitler et al. | |
| 2002/0055720 A1 | 5/2002 | Hohlfelder et al. | |
| 2003/0233070 A1 | 12/2003 | De La Serna et al. | |
| 2004/0116847 A1 | 6/2004 | Wall | |
| 2004/0225276 A1 | 11/2004 | Burgess | |
| 2005/0070848 A1 | 3/2005 | Kim et al. | |
| 2005/0085767 A1 | 4/2005 | Menassa | |
| 2005/0165368 A1 | 7/2005 | Py et al. | |
| 2005/0267403 A1 | 12/2005 | Landau et al. | |
| 2005/0272615 A1 | 12/2005 | Bitler | |
| 2006/0264967 A1* | 11/2006 | Ferreyro et al. | 606/93 |
| 2007/0055200 A1 | 3/2007 | Gilbert | |
| 2007/0088267 A1 | 4/2007 | Shekalim | |
| 2007/0149925 A1 | 6/2007 | Edwards et al. | |
| 2007/0287958 A1 | 12/2007 | McKenzie et al. | |
| 2009/0076477 A1 | 3/2009 | Schneider et al. | |
| 2009/0177158 A1 | 7/2009 | Krumme et al. | |
| 2009/0240200 A1 | 9/2009 | Heneveld et al. | |

FOREIGN PATENT DOCUMENTS

| | | | |
|---|---|---|---|
| WO | 03/061508 A1 | 7/2003 | |
| WO | 2004/067067 A1 | 8/2004 | |
| WO | 2007/028253 A2 | 3/2007 | |
| WO | 2007/126532 A2 | 11/2007 | |
| WO | 2008/066657 A2 | 6/2008 | |
| WO | 2009/021020 A1 | 2/2009 | |
| WO | 2009/023035 A1 | 2/2009 | |
| WO | 2009/086250 A1 | 7/2009 | |

OTHER PUBLICATIONS

Indian Journal of Dermatology, Venereology and Leprology, Soft Tissue Augmentation—Use of Hyaluronic Acide as Dermal Filler, website article, Sep. 3, 2010.
EFD, Inc., HP7x, User's Guide, 2004.
EFD, Inc., Performus II, III, IV, V, VI, VII, VIII Dispensing Systems, User's Guide, 2007.
Kreiger Ra et al., CO2 Power-Assisted Hand-Held Syringe: Better Visualization During Diagnostic and Interventional Angiography, Cathet Cardiovasc Diagn. Nov. 1990;21(3):213.
Threepharm Medical, "News—Optistat® Handheld Power Injector"; www.threepharm.ro/medical/news.php; website, Jun. 15, 2009.
Tulip Products, CellFriendly(TMM)—A Success Story, Brochure, 2010.
EFD, Inc., Extra Dispensing Power in the Palm of Your Hand, brochure, 2006.
EFD, Inc., Performus II Dispenser, Brochure, 2007.
EFD, Inc., New Mikros Dispense Pen System for Consistent Microdot Control, Brochure, 2006.
EFD, Inc., High-Pressure Dispensing Tool Simplifies Haptics Attachment, No. 42, 2006.
EFD, Inc., Mikros User's Guide, 2006.
EFD, Inc., HP4x User's Guide, 2003.
EFD, Inc., Hand-Operated Dispense Valves, Brochure, 2006.
EFD, Inc., Ultra 2400 Series, Dispensing Workstation, User's Guide, 2008.
EFD, Inc., Ultra 2400 Series, Dispensing Workstation, Brochure, 2006.
EFD, Inc., Ultra 1400 Series, Dispenser, Brochure, 2008.
U.S. Patent and Trademark Office, Office Action in U.S. Appl. No. 12/477,527, Nov. 5, 2009.
U.S. Patent and Trademark Office, International Search Report and Written Opinion in PCT Serial No. PCT/US08/87910, Mar. 16, 2009.
U.S. Patent and Trademark Office, International Search Report and Written Opinion in PCT Serial No. PCT/US08/072310, Nov. 7, 2008.
Korean Intellectual Property Office, International Search Report in PCT Serial No. PCT/US2007/023226, May 20, 2008.
The International Bureau of WIPO, International Preliminary Report on Patentability in PCT Serial No. PCT/US2007/023226, May 5, 2009.
Slautterback, JR-1 Hotmelt System, Brochure, Nov. 1998.
Tulip Products, CellFriendly(TM)—A Success Story, Brochure, 2010.
Adhesive Technologies, Inc., The Ad-Tech(TM) MBS Hot Melt Mini-Bulk System, Brochure, Oct. 1998.
Nordson Corporation, Drawing of Model 656501, Hand Gun Assembly, Nov. 2000.

* cited by examiner

# APPARATUS AND METHODS FOR INJECTING HIGH VISCOSITY DERMAL FILLERS

CROSS-REFERENCE TO RELATED APPLICATIONS

This application is a continuation of U.S. application Ser. No. 12/114,194, entitled "Apparatus and Methods for Injecting High Viscosity Dermal Fillers", filed May 2, 2008 now abandoned (pending) which is a continuation-in-part of International Patent Application No. PCT/US2007/023226, entitled "Compositions, Devices and Methods for Modifying Soft Tissue," filed Nov. 1, 2007 (expired), which claims priority to U.S. Provisional Application Ser. No. 60/856,430, entitled "Soft Tissue Modification," filed Nov. 3, 2006 (expired), U.S. Provisional Application Ser. No. 60/857,546, entitled "Soft Tissue Modification," filed Nov. 8, 2006 (expired), and U.S. Provisional Application Ser. No. 60/857,755, entitled "Injection Device," filed Nov. 8, 2006 (expired), each of which is incorporated herein by reference in its entirety.

This application is a continuation of U.S. Application Serial No. 12/114,194, entitled "Apparatus and Methods for Injecting High Viscosity Dermal Fillers", filed May 2, 2008 (pending) which claims priority to U.S. Provisional Application Ser. No. 60/964,066, entitled "Controlled Injection Device," filed Aug. 8, 2007 (expired), which is incorporated herein by reference in its entirety, and claims priority to U.S. Provisional Application Ser. No. 60/993,541, entitled "Controlled Injection Device," filed Sep. 12, 2007 (expired), which is incorporated herein by reference in its entirety, and claims priority to U.S. Provisional Application Ser. No. 61/016,223, entitled "Self-Contained Pressurized Injection Device," filed Dec. 21, 2007 (expired), which is incorporated herein by reference in its entirety.

BACKGROUND

The invention relates generally to medical devices and methods, and more particularly to medical devices and methods for injecting high viscosity dermal fillers into a body.

High viscosity medicaments, such as dermal fillers, can be injected into the body to augment soft tissue portions within the body. For example, high viscosity compositions can be injected adjacent the urinary sphincter muscle to increase the volume of the tissue within the urinary tract to treat urinary incontinence. High viscosity compositions can also be injected into the skin to change the contour of and/or increase the volume of the skin. For example, known high viscosity compositions can be injected within facial skin to remove wrinkles, treat scars or the like.

Some known procedures for injecting high viscosity dermal fillers include injecting the dermal filler using a standard syringe. In such procedures, the force and/or pressure required to convey the dermal filler from the syringe body through the needle can be generated manually by having the user manually depress a plunger into the syringe body. The force generated by manually depressing a plunger, however, can be sporadic, thus resulting in undesirable fluctuations in the flow of the dermal filler through the needle, which can result in the user injecting more or less dermal filler at a particular location within the body than is desired. Generating the injection force and/or pressure manually can also result in inconsistent results between different users. Moreover, in certain situations, the force generated by manually depressing a plunger can be insufficient to provide the desired flow rate of dermal filler. Additionally, because the total volume of dermal filler injected is a function of the length of travel of the plunger, it can be difficult to deliver a sufficient volume of dermal filler when injecting the dermal filler manually using a standard syringe. Moreover, generating the injection force and/or pressure manually can result in user fatigue and/or chronic health problems for the user, such as, for example arthritis.

Thus, a need exists for improved apparatus and methods for injecting high viscosity dermal fillers into a body.

SUMMARY

Medical injectors and methods of injecting high viscosity dermal fillers are described herein. In some embodiments, a method includes inserting a distal end portion of a needle of a medical injector into a skin of a body. An energy source operatively coupled to the medical injector is actuated such that a dermal filler is conveyed from the medical injector into the skin through the distal end portion of the needle. The distal end portion of the needle is moved within the skin during the actuating.

DETAILED DESCRIPTION

In some embodiments, a method includes inserting a distal end portion of a needle of a medical injector into a skin of a body. The skin can include, for example, facial skin. An energy source operatively coupled to the medical injector is actuated such that a dermal filler is conveyed from the medical injector into the skin through the distal end portion of the needle. The energy source can include, for example, a pressurized fluid configured to move a piston within the medical injector. The distal end portion of the needle is moved within the skin during the actuating. In some embodiments, a non-manually-powered machine operatively coupled to the medical injector is actuated such that a dermal filler is conveyed from the medical injector into the skin through the distal end portion of the needle. Optionally, the method can include regulating a flow rate of the dermal filler through the distal end portion of the needle during the actuating.

As used herein, the words "proximal" and "distal" refer to direction closer to and away from, respectively, an operator (e.g., surgeon, physician, nurse, technician, etc.) of the medical device. Thus, for example, the end of the medicament delivery device contacting the patient's body would be the distal end of the medicament delivery device, while the end opposite the distal end would be the proximal end of the medicament delivery device.

As used herein, the words "non-manual" or "non-manually" are used to describe an operation and/or an apparatus in which a source of energy and/or a force for carrying out the operation and/or a function of the apparatus is not directly produced by a human. For example, an apparatus for non-manually injecting a dermal filler can include any apparatus in which the force to inject the dermal filler is not directly produced by a human. Examples of a non-manual injection apparatus include an apparatus having a compressed gas source to provide the injection force, an apparatus having a spring to provide the injection force, and an apparatus having an electric motor to provide the injection force. An apparatus for non-manually injecting a dermal filler, however, can include a manual actuator (e.g., an on/off switch, a push button, a foot pedal or the like) to initiate the non-manual injection.

Figure 1:
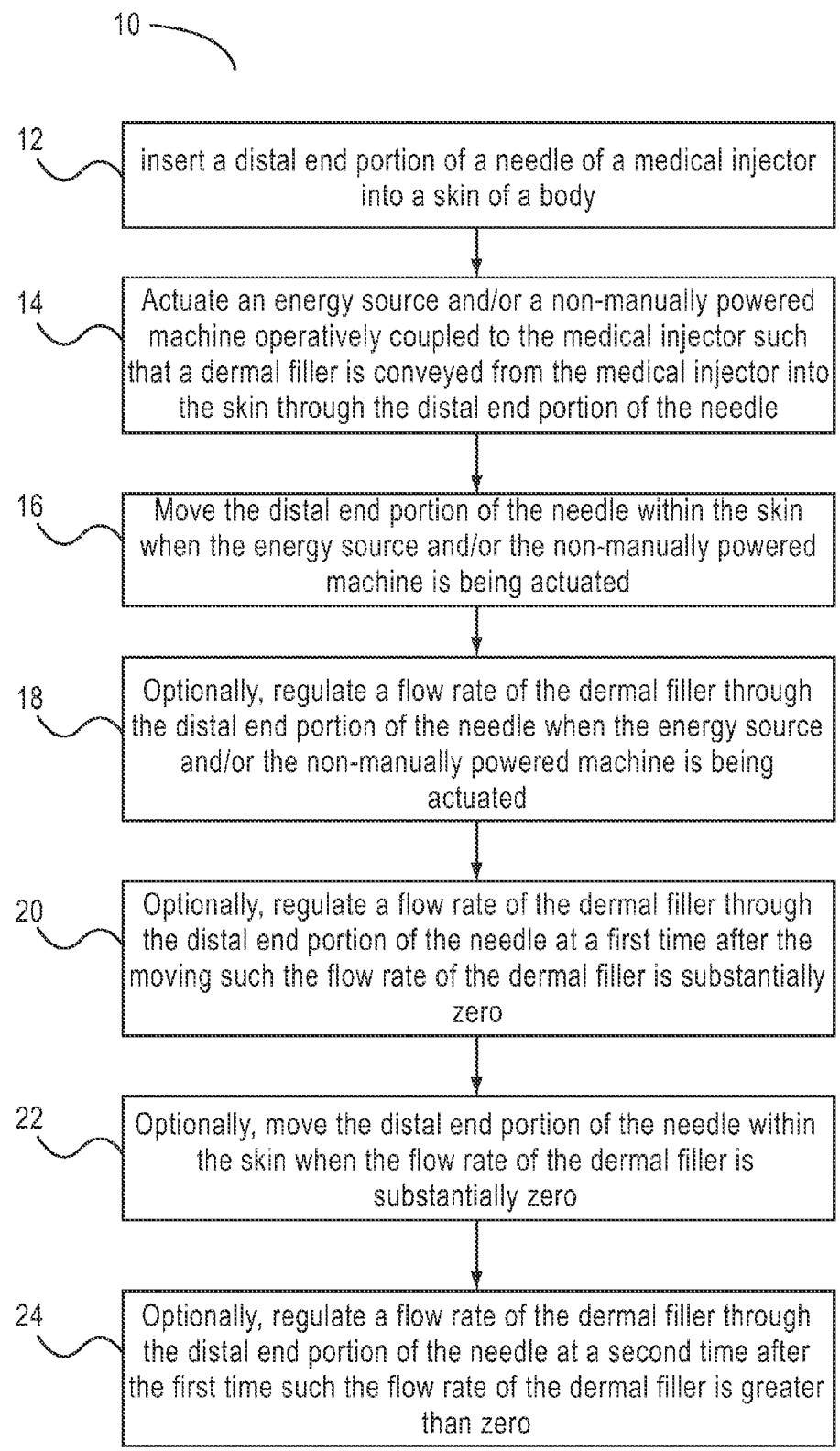
FIG. 1 is a flow chart illustrating a method of assembling a medical injector according to an embodiment.
Figure 2:
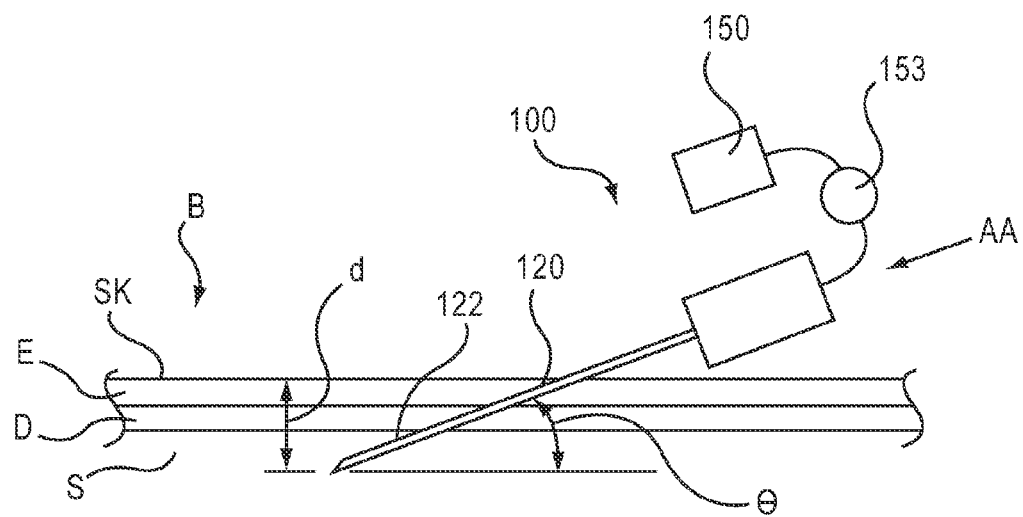
FIGS. 2-4 are schematic illustration showing a portion of a body B containing a dermal filler in a first configuration, a second configuration and a third configuration, respectively, according to the method illustrated in FIG. 1.
Figure 3:
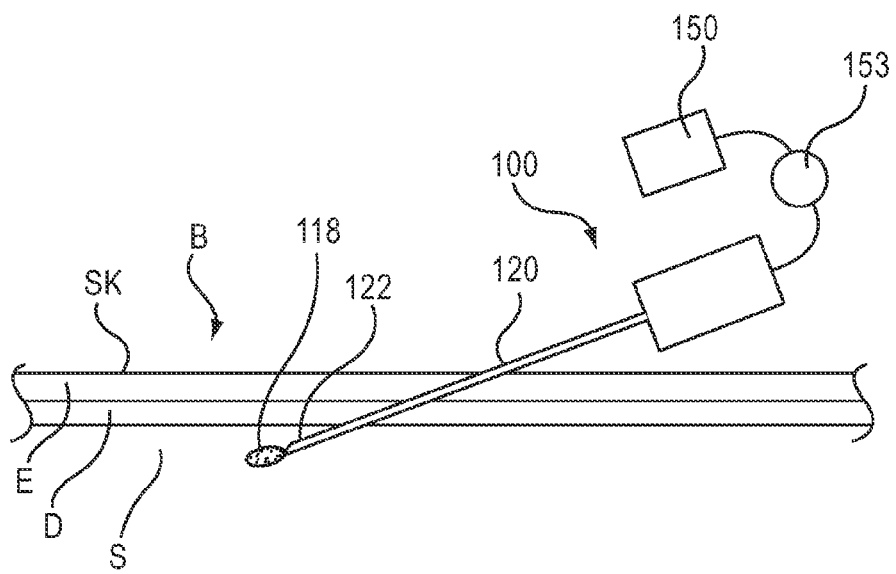
Figure 4:
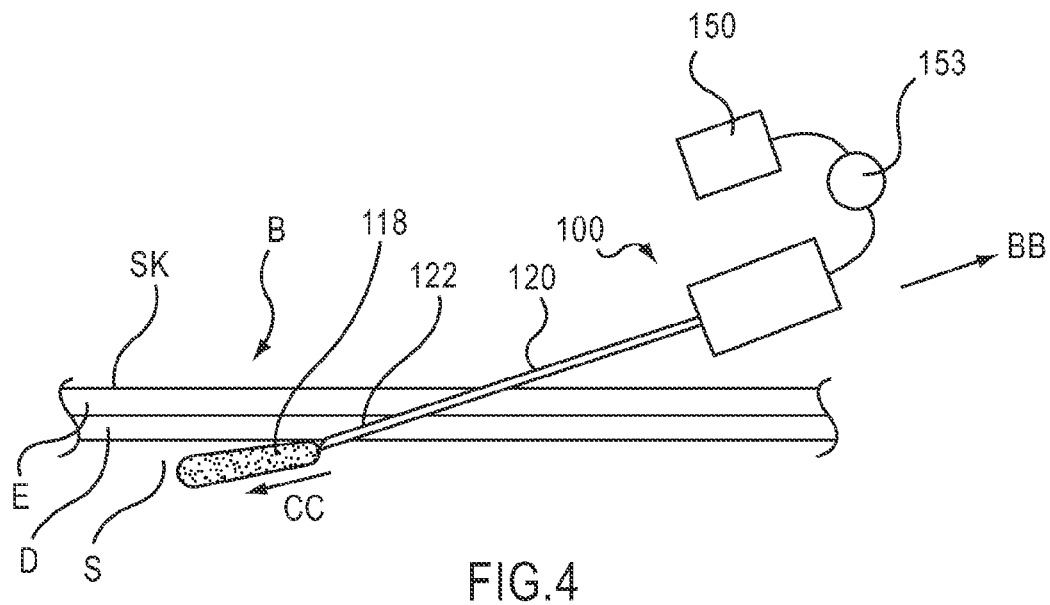

FIG. 1 is a flow chart illustrating a method 10 of injecting a dermal filler according to an embodiment. FIGS. 2-4 are schematic illustrations showing a portion of a body B containing a dermal filler 118 injected therein according to the method 10, in a first configuration, a second configuration and a third configuration, respectively. As shown in FIG. 1, the illustrated method includes inserting a distal end portion of a needle of a medical injector into a skin of a body, at 12. The skin can be disposed at any location of the body, such as for example, facial skin. Referring to FIG. 2, the distal end portion 122 of the needle 120 is inserted into the skin SK in a distal direction as shown by the arrow AA. The needle 120 is inserted into the skin SK at an angle Θ relative to the surface of the skin SK and at depth d within the body B. The needle 120 can be inserted into the skin SK at any suitable angle Θ and at any suitable depth d for achieving the desired result. In some embodiments, for example, the needle 120 is inserted into the skin SK at an angle Θ of between 5 and 35 degrees. In other embodiments, the needle 120 is inserted into the skin SK at an angle Θ of approximately 20 degrees. In some embodiments, for example, the needle 120 is inserted into the skin SK at a depth d of between 1.5 and 6 millimeters. In other embodiments, the needle 120 is inserted into the skin SK at a depth d of between approximately 1.5 and 2 millimeters.

Although the distal end portion 122 of the needle 120 is shown as being inserted into the subcutaneous tissue S of the skin SK, in some embodiments, the distal end portion 122 of the needle 120 can be inserted into the epidermis E and/or the dermis D of the skin SK. In other embodiments, the distal end portion 122 of the needle 120 can be inserted below the subcutaneous tissue S. In yet other embodiments, the distal end portion 122 of the needle 120 can be inserted through the skin SK into another portion of the body B, such as for example a urinary sphincter (not shown in FIGS. 2-5).

Returning to the flow chart shown in FIG. 1, an energy source operatively coupled to the medical injector is actuated such that a dermal filler is conveyed from the medical injector into the skin through the distal end portion of the needle, at 14. As shown in FIG. 3, the energy source 150 is actuated via an actuator 153. The energy source 150 can include any suitable form of energy that can act upon the medical injector 100 to convey the dermal filler 118 from the medical injector 100 through the distal end portion 122 of the needle 120. For example, in some embodiments, the energy source 150 can include a pressurized gas that exerts a force on a portion of the medical injector 100. When the energy source 150 is actuated by the actuator 153, the dermal filler 118 is conveyed from the medical injector 100 through the distal end portion 122 of the needle 120. In this manner, the dermal filler 118 can be injected into the body B non-manually. Said another way, the dermal filler 118 can be injected into the body B without the user producing the energy necessary for the injection.

Returning to the flow chart shown in FIG. 1, the distal end portion of the needle is moved within the skin when the energy source is being actuated, at 16. In this manner, the user can vary the location of the distal end portion of the needle within the skin when the dermal filler is being injected into the body B. As shown in FIG. 4, the distal end portion 122 of the needle 120 is moved in a proximal direction, as shown by the arrow BB, when the energy source 150 is being actuated. In this manner, the user can inject a substantially continuous bead of dermal filler 118 along a desired passageway (e.g., a wrinkle) within the skin SK. More particularly, the distal end portion 122 of the needle 120 is moved in a direction substantially opposite the direction of flow of the dermal filler 118 from the distal end portion 122 of the needle 120 (shown by the arrow CC in FIG. 4).

Because the dermal filler 118 is conveyed from the distal end portion 122 of the needle 120 non-manually, the user is not burdened with producing a force in the distal direction (to inject the dermal filler 118) while simultaneously moving the distal end portion 122 of the needle 120 in the proximal direction. In this manner, the operation of producing a force to inject the dermal filler 118 is independent from the operation of moving the distal end portion 122 of the needle 120. Similarly stated, the operation of producing a force to inject the dermal filler 118 is decoupled from (i.e., is separate and distinct from) the operation of moving the distal end portion 122 of the needle 120. This arrangement can result in a repeatable, continuous and/or controlled movement of the distal end portion 122 of the needle 120 and/or injection of the dermal filler 118. In contrast, some known medical injectors require the user to use the same hand to produce a force in a distal direction along a longitudinal axis of the medical injector to inject a dermal filler and move the needle along the longitudinal axis, for example, in an opposite (i.e., proximal) direction. In such instances, the injection of the dermal filler can be irregular, uncontrolled and/or discontinuous. Moreover, the disadvantage of such manual injection procedures can be exacerbated when injecting high viscosity dermal fillers, because, as described herein, the force to inject such dermal fillers can be in excess of approximately 4.5 N (10 lbf). For example, when injecting high viscosity dermal fillers using known medical injectors, it can be difficult for the user to maintain the force necessary to inject the dermal filler at the desired flow rate throughout the injection event. Thus, when injecting high viscosity dermal fillers using known medical injectors, the resulting bead of dermal filler can have undesirable spatial variability in its size and/or volume.

Although the distal end portion 122 of the needle 120 is shown and described above as being moved in the proximal direction when the energy source 150 is being actuated, in other embodiments, the distal end portion 122 can be moved in any manner. For example, in some embodiments the distal end portion 122 of the needle 120 can be moved in a distal direction (i.e., in substantially the same direction as the flow of the dermal filler 118 from the distal end portion 122 of the needle 120). In other embodiments, the distal end portion 122 of the needle 120 can be moved in a direction not parallel to a longitudinal axis of the needle 120. In yet other embodiments, the distal end portion 122 of the needle 120 can be rotated when the energy source 150 is being actuated. For example, in some embodiments, the user can "fan" the distal end portion 122 of the needle 120 (i.e., move the distal end portion 122 in a direction not parallel to a longitudinal axis of the needle 120) within the skin SK when the energy source is being actuated. Moreover, the distal end portion 122 of the needle 120 can be moved any suitable distance when the energy source 150 is being actuated. In some embodiments, for example, the distal end portion 122 of the needle 120 can be moved a distance of at least 4 millimeters during actuation of the energy source 150.

Returning to the flow chart shown in FIG. 1, in some embodiments, the method can optionally include regulating a flow rate of the dermal filler through the distal end portion of the needle when the energy source is being actuated, at 18. In this manner, the user can adjust the amount the dermal filler being injected within and/or beneath the skin to provide the desired cosmetic and/or therapeutic results. In some embodiments, for example, the flow rate of the dermal filler can be regulated to maintain a substantially constant flow rate of the dermal filler through the distal end portion of the needle when the distal end portion of the needle is moved within and/or beneath the skin. Said another way, in some embodiments, the flow rate of the dermal filler can be regulated to produce a substantially uniform bead of dermal filler within the skin. In some embodiments, for example, the flow rate of the dermal filler can be regulated when the needle is moved within the skin to produce a substantially uniform bead of dermal filler having a volume of approximately 1 to 2 cubic centimeters and a length of between approximately 4 millimeters and 13 millimeters. In other embodiments, the flow rate of the dermal filler can be regulated when the needle is moved within the skin to produce a substantially uniform bead of dermal filler having a volume of less than 1 cubic centimeter and a length of between approximately 4 millimeters and 13 millimeters. For example, in some embodiments, the flow rate of the dermal filler can be regulated when the needle is moved within the skin to produce a substantially uniform bead of dermal filler having a volume of approximately 0.1 to 0.2 cubic centimeter and a length of between approximately 4 millimeters and 13 millimeters. In yet other embodiments, the flow rate of the dermal filler can be regulated when the needle is moved within the skin to produce a substantially uniform bead of dermal filler having a volume of greater than 2 cubic centimeter (e.g., a volume of 3, 4, 5, or 10 cubic centimeters) and a length of up to 150 millimeters. Such a bead can be used, for example, to increase the skin volume in the areas of the nasal labial fold, the jowls and/or the neck region, and can smooth the appearance of wrinkles in those areas.

The flow rate of the dermal filler can be regulated to produce any suitable flow rate. For example, in some embodiments, the flow rate of the dermal filler can be regulated to a substantially constant flow rate of at least approximately 0.02 cubic centimeters per minute. In other embodiments, the flow rate of the dermal filler can be regulated to a substantially constant flow rate of between approximately 0.02 cubic centimeters per minute and 0.5 cubic centimeters per minute. In yet other embodiments, the flow rate of the dermal filler can be regulated to a substantially constant flow rate of as much as 3 cubic centimeters per minute. In still other embodiments, the flow rate of the dermal filler can be regulated to a substantially constant flow rate greater than 3 cubic centimeters per minute.

Figure 5:
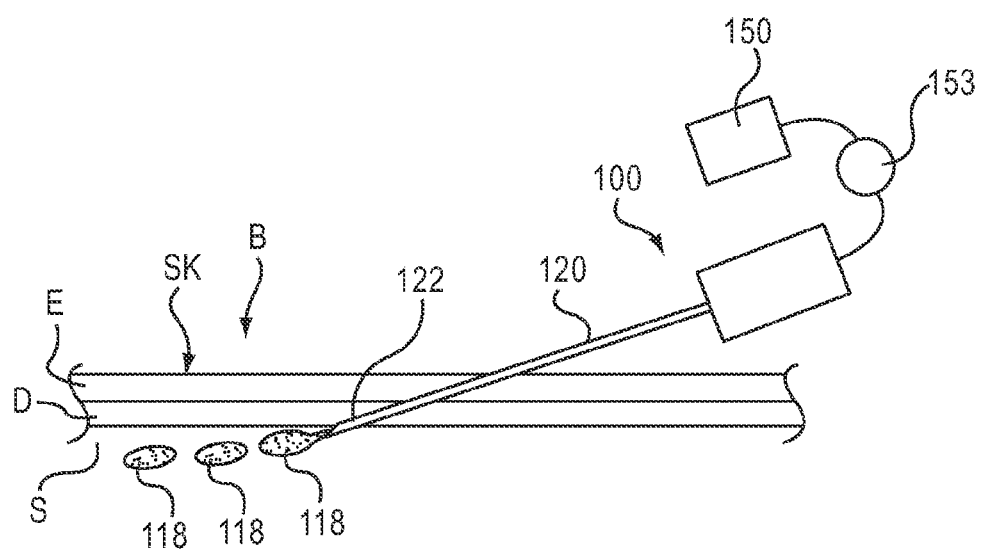
FIG. 5 is schematic illustration showing a portion of a body B containing a dermal filler injected therein by a method according to an embodiment.

Although the flow rate of the dermal filler through the distal end portion of the needle is described above as being regulated to a substantially constant value when the needle is moved within the body, in some embodiments, the flow rate of the dermal filler can be selectively varied during the injection process. In this manner, the user can produce a bead and/or set of beads of dermal filler within the skin having spatially varied volume. Moreover, referring to the flow chart in FIG. 1, in some embodiments, the method 10 can include optionally regulating a flow rate of the dermal filler through the distal end portion of the needle such that the flow rate is substantially zero at a first time after the needle has been moved and still remains in the skin, at 20. Said another way, in some embodiments, the method 10 can include optionally stopping the flow of the dermal filler through the distal end portion of the needle after the needle has been moved within the skin. The distal end portion of the needle can then be moved while the flow rate of the dermal filler through the distal end portion of the needle is zero, at 22. The flow rate of the dermal filler through the distal end portion of the needle can then be regulated such that the flow rate is increased greater than zero, at 24. In this manner, the user can produce a discontinuous bead and/or set of beads of dermal filler within the skin, as shown in FIG. 5. In some embodiments, for example, the flow rate of the dermal filler through the distal end portion of the needle can be regulated such that at least one discrete bead from the set of beads has a volume of approximately 0.1 cubic centimeters or less. In other embodiments, the flow rate of the dermal filler through the distal end portion of the needle can be regulated such that at least one discrete bead from the set of beads has a volume of less than approximately 0.01 cubic centimeters or less. In some embodiments, the flow rate of the dermal filler through the distal end portion of the needle can be regulated to produce such a set of discontinuous beads in areas of the skin surrounding the eye.

As described in more detail herein, the flow rate of the dermal filler through the distal end portion of the needle can be regulated in any suitable manner. For example, referring to FIGS. 2-4, in some embodiments, the flow rate of the dermal filler 118 through the distal end portion 122 of the needle 120 can be regulated by selectively controlling the energy from the energy source 150 to the medical injector 100. Said another way, in some embodiments, the flow rate of the dermal filler 118 through the distal end portion 122 of the needle 120 can be regulated by mechanisms outside of the flow path of the dermal filler 118. Moreover, in some embodiments, the flow rate of the dermal filler 118 through the distal end portion 122 of the needle 120 can be regulated via the actuator 153. For example, in some embodiments, the user can repeatedly and/or controllably actuate the energy source 150 using the actuator 153. Said another way, in some embodiments, the user can repeatedly toggle the actuator 153 to selectively couple the energy source 150 to and decouple the energy source 150 from the medicament injector 100. In this manner, for example, the flow rate of the dermal filler can be regulated to produce a discontinuous bead and/or set of beads of dermal filler within the skin, as described above.

In other embodiments, the flow rate of the dermal filler 118 through the distal end portion 122 of the needle 120 can be regulated by selectively restricting the flow path of the dermal filler 118 within the medical injector 100 and/or the needle 120. For example, in some embodiments, the flow rate of the dermal filler 118 through the distal end portion 122 of the needle 120 can be regulated by a valve within the medicament flow path.

Figure 6:
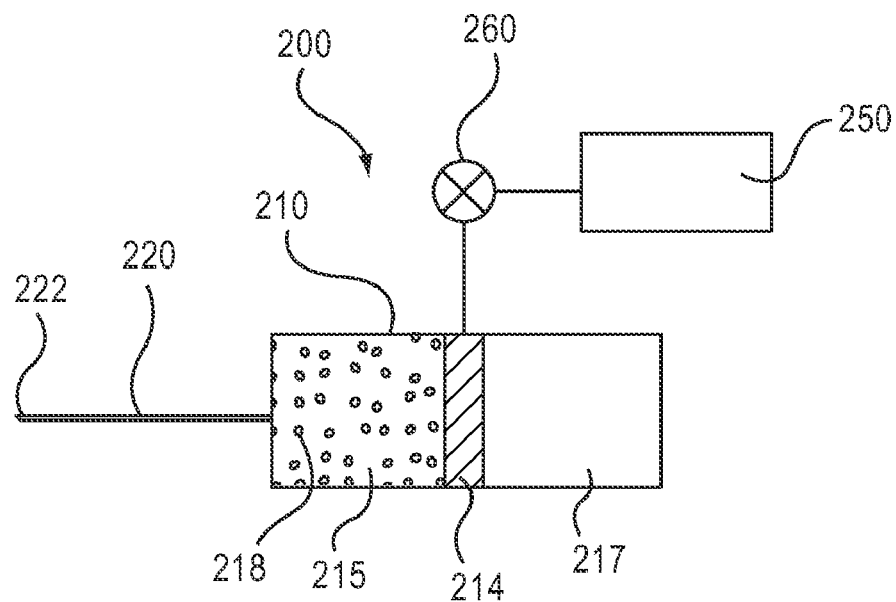
FIGS. 6 and 7 are schematic illustrations of a medical device according to an embodiment, in a first configuration and a second configuration, respectively.
Figure 7:
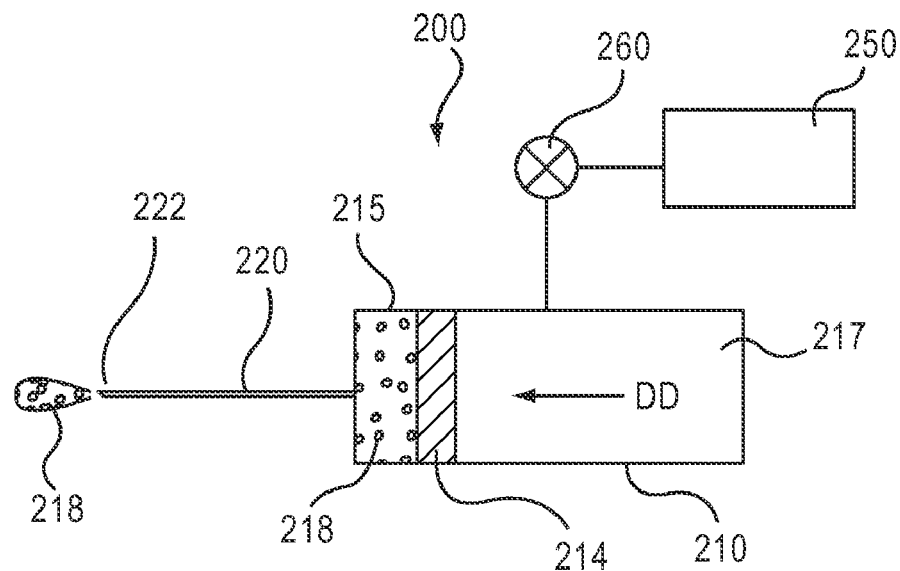

FIGS. 6 and 7 are schematic illustrations of a medical device 200, according to an embodiment configured inject a medicament 218. The medical device 200 includes a medicament container 210, a needle 220, an energy source 250 and a regulator 260. The medicament container 210 includes a piston 214 movably disposed therein, such that the medicament container 210 is divided into a first portion 215 and a second portion 217. In some embodiments, for example, the piston 214 can be disposed within the medicament container 210 such that the first portion 215 of the medicament container 210 is fluidically isolated from the second portion 217 of the medicament container 217.

The first portion 215 of the medicament container 210 is configured to contain a medicament 218 having a high viscosity (i.e., a medicament having a viscosity of at least 100 Poise). The medicament 218 can be any medicament suitable for being injected into a body. For example, in some embodiments, the medicament 218 can be a high viscosity dermal filler (e.g., a liquid dermal filler, a paste-like dermal filler, a dermal filler including both a liquid component and a solid component, or the like). In some embodiments, the medicament 218 can have a viscosity of at least 1000 Poise (100 N-sec/m$^2$). In other embodiments, the medicament 218 can have a viscosity of at least 10,000 Poise. In yet other embodiments, the medicament 218 can have a viscosity of at least 100,000 Poise.

In some embodiments, the medicament 218 can be a fluid that is characterized by a substantially linear shear stress as a function of the rate of shear strain applied thereto. Said another way, in some embodiments, the medicament 218 can be a Newtonian fluid having a viscosity that varies substantially only as a function of its temperature and pressure. In other embodiments, the medicament 218 can be a fluid that is characterized by a non-linear shear stress as a function of the rate of shear strain applied thereto. Said another way, in some embodiments, the medicament 218 can be a non-Newtonian fluid having a viscosity that varies according other factors, such as, for example, the magnitude of and/or rate of increase of a force applied to the medicament 218.

The needle 220 is coupled to the medicament container 210 such that the needle 220 is in fluid communication with the first portion 215 of the medicament container 210. The needle 220 can be coupled to the medicament container 210 by any suitable mechanism. For example, in some embodiments, the needle 220 can be coupled to the medicament container 210 by a Luer fitting that provides a substantially fluid-tight seal (i.e., a seal that that substantially prevents a liquid and/or a gas from passing therethrough) between the needle 220 and the medicament container 210. In some embodiments, the fluid-tight seal can be a hermetic seal (i.e., a seal that substantially prevents a gas from passing therethrough).

The needle 220 can have any suitable bore size and length. For example, in some embodiments, the needle can have a small bore to reduce patient discomfort during a procedure. For example, in some embodiments, the needle 220 can define a lumen having a nominal inner diameter of less than or equal to approximately 0.191 millimeters (i.e., a 27 gauge needle). In other embodiments, the needle 220 can define a lumen having a nominal inner diameter of less than or equal to approximately 0.140 millimeters (i.e., a 30 gauge needle). In some embodiments, for example, the needle 220 can define a lumen having a nominal inner diameter of approximately 0.114 millimeters (i.e., a 31 gauge needle). In some embodiments, for example, the needle 220 can define a lumen having a nominal inner diameter of approximately 0.089 millimeters (i.e., a 32 gauge needle). In some embodiments, the needle 220 can have a length of at least 17 millimeters.

When the piston 214 moves within the medicament container 210, as shown by the arrow DD in FIG. 7, the medicament 218 is conveyed from the first portion 215 of the medicament container 210. Said another way, a user can inject the medicament 218 into a body by actuating the medical device 200 to cause the piston 214 to move distally within the medicament container 210. As shown in FIGS. 6 and 7, the energy source 250 is operatively coupled to the piston 214 such that the piston 214 can be moved non-manually. The energy source 250 can be any suitable form of energy configured produce kinetic energy to move the piston 214 within the medicament container 210. The amount of kinetic energy required to move the piston 214 within the medicament container 210 is dependent on, among other things, the viscosity of the medicament 218, the desired flow rate of the medicament 218 through the distal end portion 222 of the needle 220, the length of the needle 220 and/or the size of the lumen defined by the needle 220. In some embodiments, the energy source 250 can produce kinetic energy sufficient to move the piston 214 such that a medicament 218 having a viscosity of at least 1000 Poise can be injected through the distal end portion 222 of the needle at a flow rate of at least 0.02 cubic centimeters per minute. In other embodiments, the energy source 250 can produce kinetic energy sufficient to move the piston 214 such that a medicament 218 having a viscosity of at least 1000 Poise can be injected through the distal end portion 222 of the needle at a flow rate of at least 0.5 cubic centimeters per minute. In yet other embodiments, the energy source 250 can produce kinetic energy sufficient to move the piston 214 such that a medicament 218 having a viscosity of at least 10,000 Poise can be injected through the distal end portion 222 of the needle 220 at a flow rate of at least 0.5 cubic centimeters per minute. In still other embodiments, the energy source 250 can produce kinetic energy sufficient to move the piston 214 such that a medicament 218 having a viscosity of at least 10,000 Poise can be injected through the distal end portion 222 of the needle 220 at a flow rate of at least 3 cubic centimeters per minute. In still other embodiments, the energy source 250 can produce kinetic energy sufficient to move the piston 214 such that a medicament 218 having a viscosity of at least 10,000 Poise can be injected through the distal end portion 222 of the needle 220 at a flow rate of between 3 and 5 cubic centimeters per minute.

Additionally, the pressure of the medicament 218 within the medicament container 210 during an injection event is related to the kinetic energy applied to the piston 214, and is therefore also dependent on, among other things, the viscosity of the medicament 218, the desired flow rate of the medicament 218 through the distal end portion 222 of the needle 220, the length of the needle 220 and/or the size of the lumen defined by the needle 220. In certain circumstances, the pressure of the medicament 218 within the medicament container 210 can be modeled by the Hagen-Poiseuille law, as indicated below:

$$P = (8 * \mu * L * Q)/(\Pi * R^4)$$

where P is the pressure of the medicament 218 within the medicament container, $\mu$ is the viscosity of the medicament 218, L is the length of the needle 220, Q is the flow rate of the medicament 218 through the distal end portion 222 of the needle 220, and R is the radius of the lumen defined by the needle 220. Because the pressure required to inject a high viscosity fluid through a small-bore needle is proportional to the inverse of the radius of the lumen of the needle to the fourth power, the pressure of the medicament 218 within the medicament container 210 necessary to achieve the desired flow rate can, at times, be relatively high. In some embodiments, the energy source 250 can be configured to move the piston 214 within the medicament container 210 such that a pressure of the medicament 218 within the medicament container 210 is greater than 345 kilopascals (50 p.s.i.). In other embodiments, the energy source 250 can be configured to move the piston 214 within the medicament container 210 such that a pressure of the medicament 218 within the medicament container 210 is greater than 690 kilopascals (100 p.s.i.). In still other embodiments, the energy source 250 can be configured to move the piston 214 within the medicament container 210 such that a pressure of the medicament 218 within the medicament container 210 is greater than 1035 kilopascals (150 p.s.i.). In still other embodiments, the energy source 250 can be configured to move the piston 214 within the medicament container 210 such that a pressure of the medicament 218 within the medicament container 210 is greater than 34.5 Megapascals (5000 p.s.i.).

The regulator 260 is configured to regulate the flow rate of the medicament 218 through the distal end portion 222 of the needle 220. In this manner, the user can adjust the flow rate of the medicament 218 through the distal end portion 222 of the needle 220. In some embodiments, for example, the regulator 260 can substantially stop the flow of the medicament 218 through the distal end portion 222 of the needle 220. In this manner, as described above, the user can discontinuously inject the medicament 218 within the body.

The regulator 260 can be any suitable mechanism for regulating the flow rate of the medicament 218 through the distal end portion 222 of the needle 220. As described above, in some embodiments, the regulator 260 can control the transmission of energy from the energy source 250 to the piston 214. In other embodiments, the regulator 260 can selectively restrict the flow path of the medicament 218 within the first portion 215 of the medicament container 210 and/or the needle 220.

Figure 8:
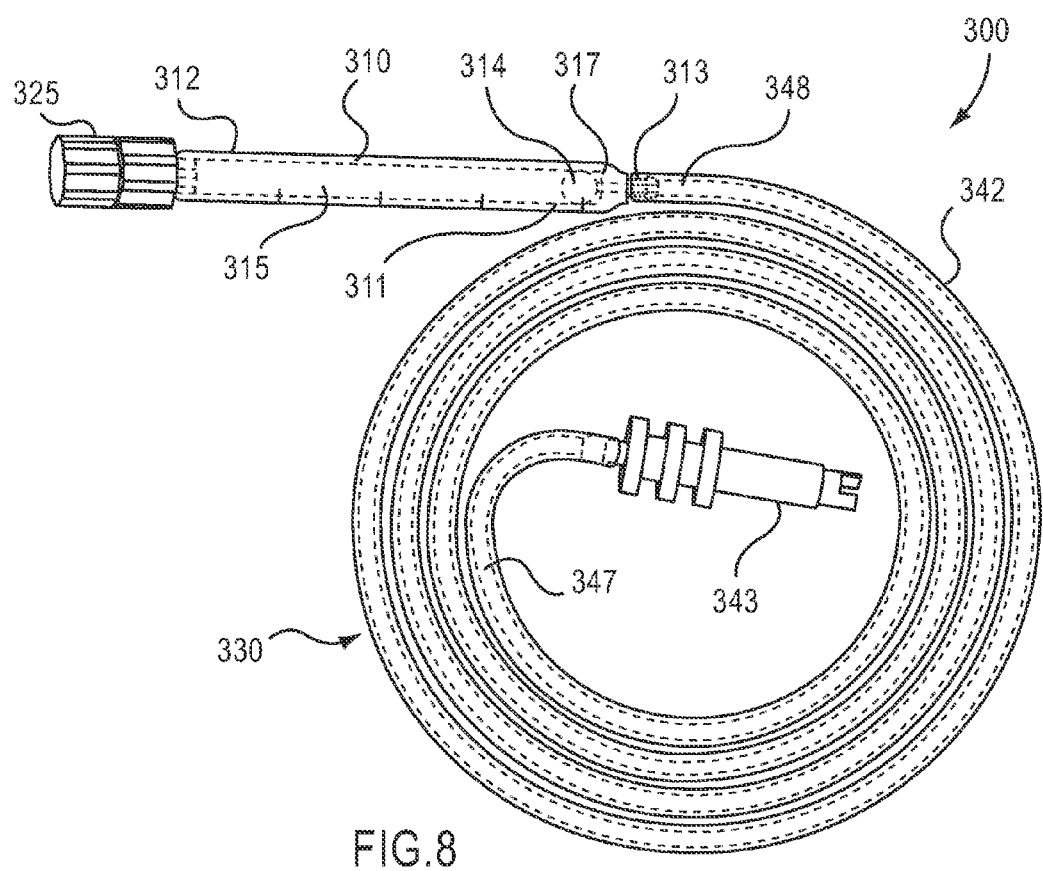
FIG. 8 is a side view of a portion of a system for injecting dermal fillers according to an embodiment.
Figure 9:
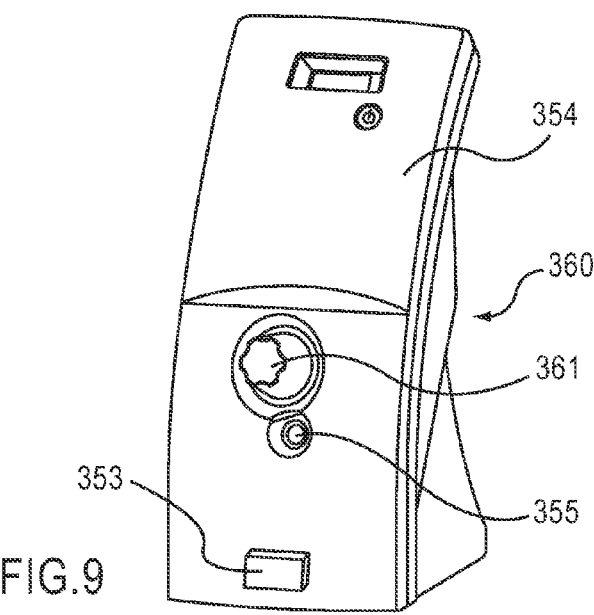
FIGS. 9 and 10 are perspective views of a portion of the system for injecting dermal fillers shown in FIG. 8.
Figure 10:
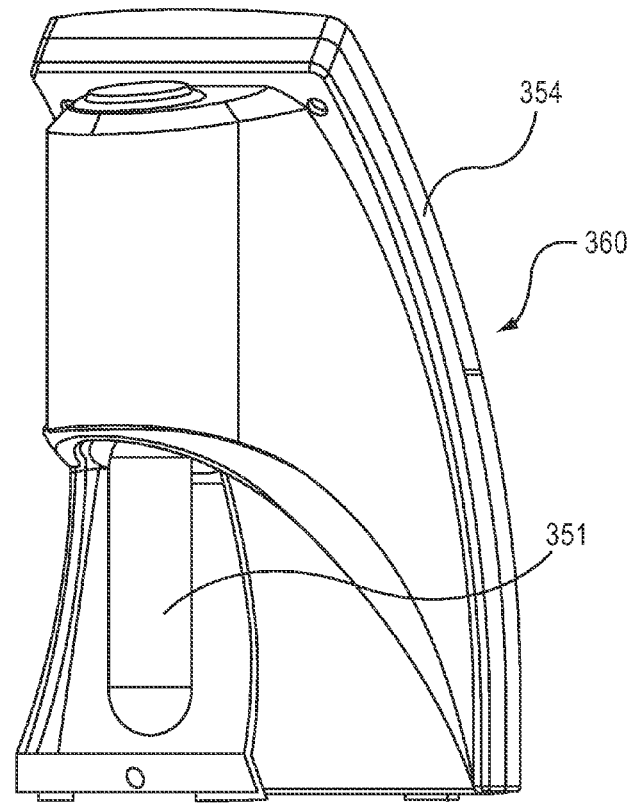

FIGS. 8-10 show a system 300 that employs a pressurized fluid to inject a dermal filler according to an embodiment. The system 300 includes a medicament container 310, a needle (not shown in FIG. 8), a source of pressurized fluid 351 (see FIGS. 9 and 10), a regulator 360 (see FIGS. 9 and 10), and an adapter 330 configured to couple the medicament container 310 to the source of pressurized fluid 351. The medicament container 310 is a substantially rigid container having a proximal end portion 311 and a distal end portion 312. The medicament container 310 includes a piston 314 movably disposed therein such that the medicament container 310 is divided into a first portion 315 and a second portion 317. The first portion 315 of the medicament container 310 is configured to contain a dermal filler 318 having a high viscosity. The medicament 318 can be any medicament suitable for being injected into a body, as described herein.

A coupler 325 is disposed at the distal end portion 312 of the medicament container 310. The coupler 325 is configured to removably couple the needle (not shown in FIG. 8) to the distal end portion 312 of the medicament container 310 such that the needle is in fluid communication with the first portion 315 of the medicament container 310. The coupler 325 can include any suitable coupling mechanism configured to produce a substantially fluid-tight coupling between the needle and the medicament container 310. For example, in some embodiments, the coupler 325 can be a Luer lock fitting that threadedly engages a hub of the needle and maintains the hub in position about a protrusion (not shown in FIG. 8) at the distal end portion 312 of the medicament container 310. In such an arrangement, the protrusion and the needle hub can have mating tapered surfaces such that a substantially fluid-tight interface is produced when the needle hub is coupled to the medicament container 310 by the coupler 325.

The adapter 330, which is configured to couple the medicament container 310 to the source of pressurized fluid 351, includes a tube 342 and a coupler 343. The tube 342 includes a proximal end portion 347 and a distal end portion 348. The distal end portion 348 of the tube 342 is disposed about a barbed fitting 313 of the medicament container 310 to couple the medicament container 310 to the adapter 330. The distal end portion 348 of the tube 342 can be secured about the barbed fitting 313, for example, by the elastic properties of the tube 342 (i.e., an interference fit between the tube 342 and the barbed fitting 313), an external clamp (not shown), an adhesive, and/or the like. The coupler 343 is coupled to the proximal end portion 347 of the tube 342, and is configured to couple the tube 342 to the source of pressurized fluid 351, as described in more detail below.

As shown in FIGS. 9 and 10, the source of pressurized fluid 351 and the regulator 360 are contained within the housing 354. In this manner, the flow rate and/or the pressure of the pressurized fluid delivered from the source of pressurized fluid 351 to the medicament container 310 can be regulated and/or actuated by the integrated assembly within the housing 354. The source of pressurized fluid 351 can include any suitable fluid (e.g., a gas or a liquid) configured to produce a pressure when conveyed to the second portion 317 of the medicament container 310, as described in more detail below. In some embodiments, for example, the source of pressurized fluid 351 can be a compressed $CO_2$ cartridge configured to be threadedly coupled to the housing 354. In other embodiments, the source of pressurized fluid 351 can include a reservoir, an accumulator and/or an adapter configured to receive a pressurized gas from an external source (i.e., a facility gas supply system).

The housing 354 includes an actuator 353, a coupler fitting 355 and a regulator knob 361. The coupler fitting 355 is configured to receive the coupler 343 of the adapter 330 such that the proximal end portion 347 of the tube 342 can be removably coupled to the housing 354. In this manner, the medicament container 310 can be coupled to the source of pressurized fluid 351. Said another way, in this manner, the piston 314 can be operatively coupled to the source of pressurized fluid 351. Said yet another way, in this manner, the second portion 317 of the medicament container 310 can be placed in a fluidic circuit with the source of pressurized fluid 351 such that the second portion 317 of the medicament container 310 can be selectively placed in fluid communication with the source of pressurized fluid 351.

The actuator 353, which can be, for example, a push button actuator, is configured to selectively place the second portion 317 of the medicament container 310 in fluid communication with the source of pressurized fluid 351. Similarly stated, the actuator 353 can selectively limit the flow rate and/or the pressure of the pressurized fluid delivered from the source of pressurized fluid 351 to the second portion 317 of the medicament container 310. In this manner, the user can actuate the actuator 353 to initiate the non-manual injection of the dermal filler 318 from the medicament container 310 through the needle (not shown in FIG. 8). As described above, because the dermal filler 318 is conveyed from the medicament container 310 non-manually, the user is not burdened with producing the energy and/or force necessary to cause the dermal filler 318 to be conveyed at the desired flow rate. This arrangement can result in a repeatable, continuous and/or controlled injection of the dermal filler 318.

Although the actuator 353 is shown as being actuated by a push button disposed on the housing 354, in other embodiments, the actuator 353 can be actuated via a foot switch (not shown in FIGS. 9 and 10) coupled to the housing 354. In such embodiments, the user can initiate the injection of the dermal filler 318 in a "hands free" manner, thereby allowing the user to use their hands to control the placement and/or the movement of the needle within the body. In such embodiments, the foot switch can be any suitable switch configured to cause the actuator 353 to selectively place the second portion 317 of the medicament container 310 in fluid communication with the source of pressurized fluid 351. The foot switch can be, for example, an electronic switch, a pneumatic switch or the like. In some embodiments, for example, the foot switch can be wirelessly coupled to the actuator 353.

The regulator knob 361 can be used to adjust the regulator 360 to selectively regulate the flow rate and/or the pressure of the pressurized fluid delivered from the source of pressurized fluid 351 to the second portion 317 of the medicament container 310 when the actuator 353 is actuated. In this manner, the flow rate of the dermal filler 318 from the medicament container 310 can be regulated. This arrangement allows the flow rate of the dermal filler 318 to be regulated without affecting the flow path of the dermal filler 318 and/or without any portion of the regulator 360 contacting the dermal filler 318.

The regulator 360 can be any suitable mechanism configured to regulate the flow rate and/or the pressure of the pressurized fluid from the source of pressurized fluid 351. For example, in some embodiments, the regulator 360 include components from an EFD® dispensing system, such as, for example, the EFD® 2400 pneumatic dispenser or the EFD® 2800 hydraulic controller manufactured by EFD, Inc. (a Nordson Company).

In some embodiments, the distal end portion 348 of the tube 342 is removably coupled to the medicament container 310. In this manner, a kit according to an embodiment can include the adapter 330 and one or more medicament containers 310 pre-filled with the dermal filler 318. For example, in some embodiments, a kit can include multiple medicament containers 310 pre-filled with different volumes of the dermal filler 318. In this manner, the user can select from among the pre-filled medicament containers 310 based on the amount of dermal filler 318 to be injected (e.g., the amount of dermal filler necessary for the desired cosmetic and/or therapeutic result). For example, in some embodiments, a kit can include pre-filled medicament containers 310 containing approximately 1 cubic centimeter, 2 cubic centimeters, 3 cubic centimeters, 5 cubic centimeters and/or 10 cubic centimeters of dermal filler 318. In other embodiments, a kit can include pre-filled medicament containers 310 containing greater than 10 cubic centimeters of dermal filler 318.

Such pre-filled medicament containers can accommodate increased volume of the dermal filler 318 by having an increased length and/or an increased inner diameter. Because the dermal filler 318 is injected non-manually, as described above, the length and/or the inner diameter of the medicament container 310 can be varied without regard to the physical limitations associated with actuating the medicament container manually. More particularly, because the dermal filler 318 is injected non-manually, the length and/or the inner diameter of the medicament container 310 can be varied independently from the distance through which an average user can manually depress a plunger and/or the force that an average user can apply when manually depressing a plunger.

In contrast, some known medical injectors are limited in the volume of dermal filler that can be contained therein because of the physical constraints imposed by manually actuating the medical injector. More particularly, some known medical injectors are configured contain a maximum of approximately 1 cubic centimeter of dermal filler. In such known manually-actuated injectors, the medicament pressure during injection is inversely proportional to the square of the inner diameter. Thus, increasing the size of the inner diameter to allow a greater volume of dermal filler to be contained within the medical injector can result in an increase in the force required to generate the desired medicament pressure. Accordingly, because the force that can be applied manually by a user is limited, increasing the size of the inner diameter is often not desirable. Similarly, the length of travel of the piston within the medicament container (i.e., the stroke of the injector) can be increased to allow a greater volume of dermal filler to be contained within the medical injector. However, the distance through which the piston can be moved is also limited based on the size of the user's hand.

Figure 11:
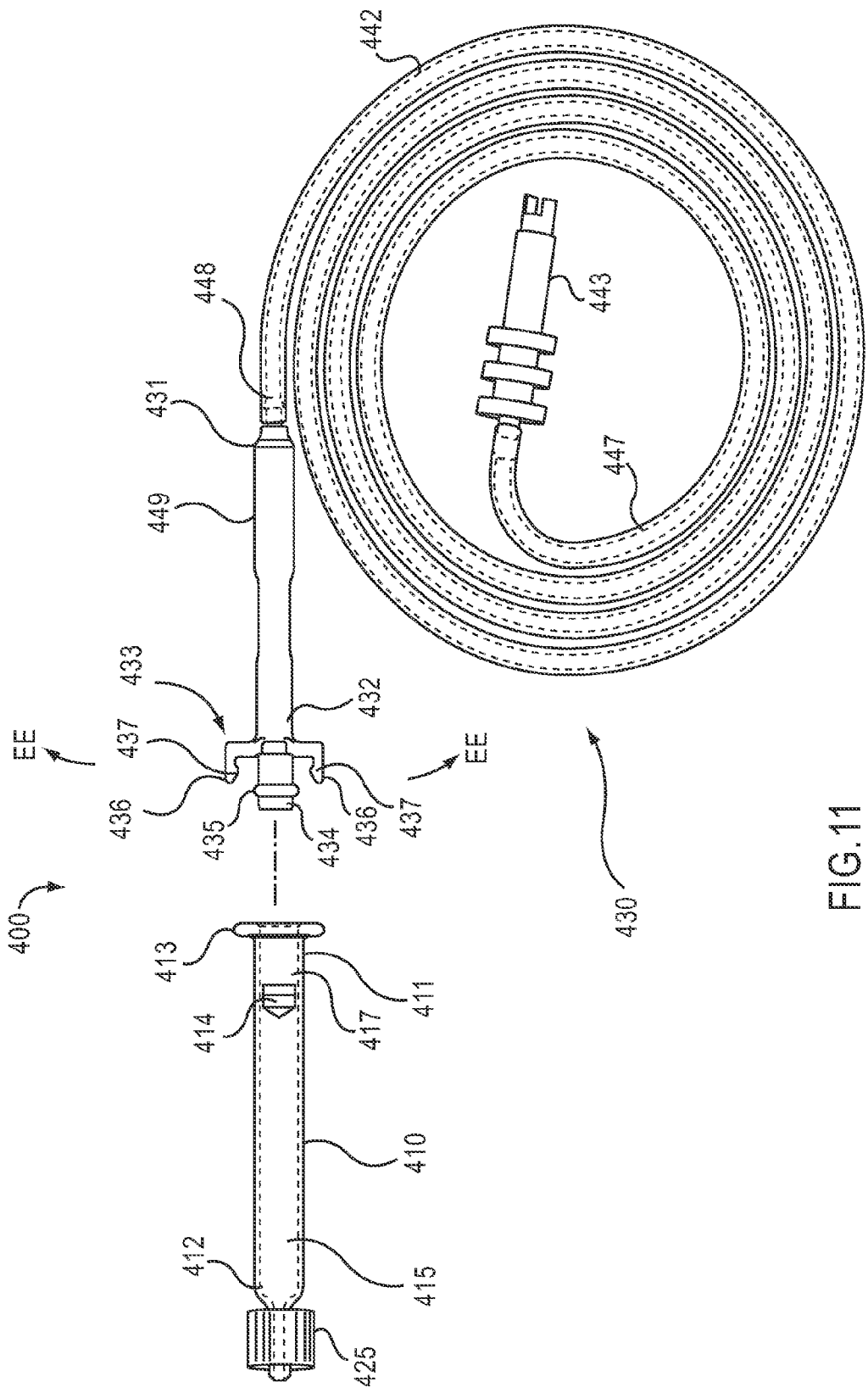
FIG. 11 is a side view of a portion of a system for injecting dermal fillers according to an embodiment.

Although the adapter 330 is shown and described above as being coupled to the medicament container 310 via the barbed fitting 313, in other embodiments, an adapter can be coupled to a medicament container having a flange. In this manner, the adapter can be configured to receive a flanged syringe. One such embodiment is shown in FIG. 11, which shows a portion of a system 400 that employs a pressurized fluid to inject a dermal filler according to an embodiment. The system 400 includes a medicament container 410, a needle (not shown in FIG. 11), a source of pressurized fluid (not shown in FIG. 11), and an adapter 430 configured to couple the medicament container 410 to the source of pressurized fluid. The source of pressurized fluid can be similar to the source of pressurized fluid 351 shown and described above. Additionally, the system 400 can include a regulator similar to regulator 360 shown and described above, and an actuator similar to the actuator 353 shown and described above. Accordingly, only the medicament container 410 and the adapter 430 are discussed in detail below.

The medicament container 410, which can be, for example, a commercially-available syringe, has a proximal end portion 411 and a distal end portion 412. The medicament container 410 includes a piston 414 movably disposed therein such that the medicament container 410 is divided into a first portion 415 and a second portion 417. The first portion 415 of the medicament container 410 is configured to contain a dermal filler 418 having a high viscosity. The medicament 418 can be any medicament suitable for being injected into a body, as described herein. A coupler 425 is disposed at the distal end portion 412 of the medicament container 410. As described above, the coupler 425 is configured to removably couple the needle (not shown in FIG. 11) to the distal end portion 412 of the medicament container 410.

The adapter 430, which is configured to couple the medicament container 410 to the source of pressurized fluid, includes a hand piece 449, a tube 442 and a coupler 443. The hand piece 449 includes a proximal end portion 431, a distal end portion 432, and an outer surface that can be contoured to assist the user in gripping and/or manipulating the hand piece 449. The distal end portion 432 of the hand piece 449 includes a coupler 433 configured to removably couple the hand piece 449 to the medicament container 410. More particularly, the coupler 433 is configured to couple the hand piece 449 to a standard, commercially-available syringe. In this manner, the adapter 430 can be used on a variety of different medicament containers 410.

The coupler 433 includes a protrusion 434, a sealing member 435, and two coupling members 436. The protrusion 434 is configured to be disposed within the second portion 417 of the medicament container 410 when the coupler 433 is coupled to the medicament container 410. The sealing member 435 is disposed about the protrusion 434 and forms a substantially fluid-tight seal between the protrusion 434 and the inner surface of the medicament container 410 when the coupler 433 is coupled to the medicament container 410. In this manner, the pressurized fluid conveyed from the source of pressurized fluid to the second portion 417 of the medicament container 410 is maintained within the second portion 417 of the medicament container 410 (i.e., the pressurized fluid does not leak out of the second portion 417 of the medicament container 410). The sealing member 435 can be, for example, an o-ring, and can be constructed from any suitable material that is compatible with the medicament 418 and/or the pressurized fluid from the source of pressurized fluid.

The coupling members 436 are disposed approximately equidistance circumferentially about the coupler 433. Said another way, the coupling members 436 are disposed approximately 180 degrees apart. In this manner the coupling members 436 engage the flange 413 of the medicament container 410 at two distinct circumferential locations when the coupler 433 is coupled to the medicament container 410. As shown in FIG. 11, each coupling member 436 includes a protrusion 437 that defines a channel within which the flange 413 of the medicament container 410 is received when the coupler 433 is coupled to the medicament container 410. More particularly, each coupling members 436 is configured to bend outwardly, as shown by the arrow EE, when pressed against the flange 413 to allow the flange 413 be disposed within the channel. When the flange 413 is disposed within the channel, the coupling members move back to their respective relaxed positions such that the flange 413 and the coupling members 436 cooperatively limit the axial movement of the medicament container 410 relative to the hand piece 449.

The tube 442 includes a proximal end portion 447 and a distal end portion 448. The distal end portion 448 of the tube 442 is coupled to the barbed fitting at the proximal end portion 431 of the hand piece 449. The distal end portion 448 of the tube 442 can be secured about the barbed fitting, for example, by the elastic properties of the tube 442 (i.e., an interference fit between the tube 442 and the barbed fitting), an external clamp (not shown), an adhesive, and/or the like. The coupler 443 is coupled to the proximal end portion 447 of the tube 442, and is configured to couple the tube 442 to the source of pressurized fluid, as described above.

Figure 12:
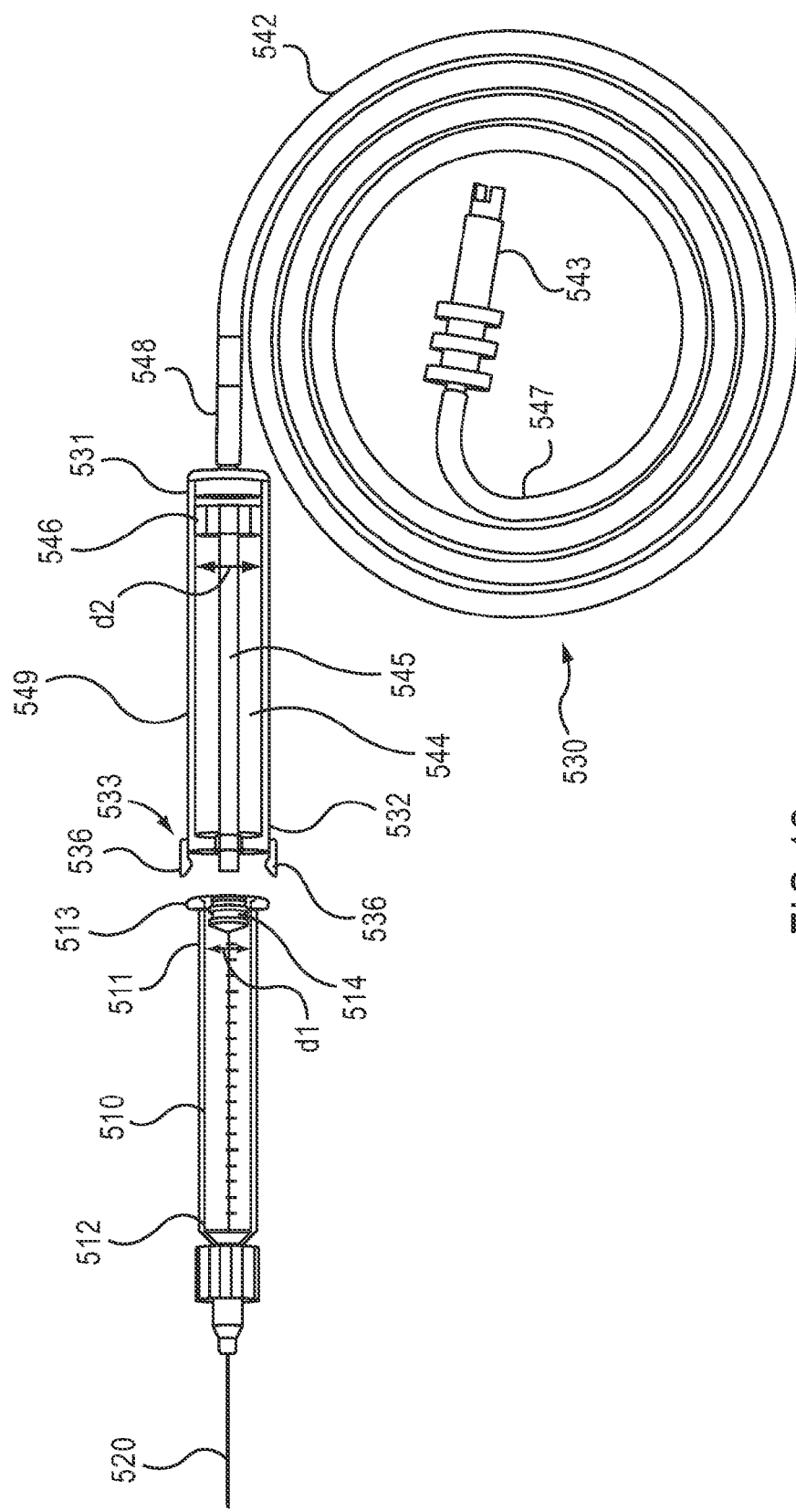
FIG. 12 is a side view of a portion of a system for injecting dermal fillers including a pressure amplifier according to an embodiment.

Although the adapter 430 is shown as being configured to convey a pressurized fluid into the second portion 417 of the medicament container 410, in other embodiments, an adapter and/or a hand piece can be configured to indirectly couple a medicament container and/or a piston to a source of pressurized fluid. For example, in some embodiments, an adapter and/or a hand piece can be configured to convert and/or amplify the pressure produced by the source of pressurized fluid to move a piston with sufficient force to generate the desired medicament flow rates and/or medicament pressure. One such embodiment is shown in FIG. 12, which shows a portion of a system 500 that employs a pressurized fluid to inject a dermal filler according to an embodiment. The system 500 includes a medicament container 510, a needle 520, a source of pressurized fluid (not shown in FIG. 12), and an adapter 530 configured to couple the medicament container 510 to the source of pressurized fluid. The source of pressurized fluid can be similar to the source of pressurized fluid 351 shown and described above. Additionally, the system 500 can include a regulator similar to regulator 360 shown and described above, and an actuator similar to the actuator 353 shown and described above. Accordingly, only the adapter 530 and the medicament container 510 are discussed below.

The medicament container 510 has a proximal end portion 511 and a distal end portion 512. The distal end portion 512 is coupled to the needle 520, as discussed above. The proximal end portion 511 is coupled to the adapter 530, as discussed below. The medicament container 510 includes a first piston 514 movably disposed therein. The first piston 514 has a diameter d1.

The adapter 530 includes a hand piece 549, a tube 542 and a coupler 543. The tube 542 includes a proximal end portion 547 and a distal end portion 548. The distal end portion 548 of the tube 542 is coupled to the proximal end portion 531 of the hand piece 549. The coupler 543 is coupled to the proximal end portion 547 of the tube 542, and is configured to couple the tube 542 to the source of pressurized fluid, as described above. In this manner, a pressurized fluid can be conveyed from the source of pressurized fluid into the hand piece 549, as described below.

The hand piece 549 includes a proximal end portion 531 and a distal end portion 532. The distal end portion 532 of the hand piece 549 includes a coupler 533 configured to removably couple the hand piece 549 to the medicament container 510. As described above, the coupler 533 includes two coupling members 536 that are disposed approximately equidistance circumferentially about the coupler 533. Said another way, the coupling members 536 are disposed approximately 180 degrees apart. In this manner the coupling members 536 engage the flange 513 of the medicament container 510 at two distinct circumferential locations when the coupler 533 is coupled to the medicament container 510.

The hand piece 549 defines a lumen 544, within which a second piston 546, having a diameter d2, and a push rod 545 are movably disposed. When the hand piece 549 is coupled to the medicament container 510 by the coupler 533, the second piston 546 is coupled to the first piston 514 by the push rod 545. Accordingly, when the hand piece 549 is coupled to the medicament container 510 by the coupler 533, a force acting on the second piston 546 is transferred directly to the first piston 514. In this manner, when a pressurized fluid from the source of pressurized fluid is conveyed into the lumen 544, the force exerted by the pressurized fluid on the second piston 546 is transferred to the first piston 514.

The corresponding pressure of the dermal filler in the medicament container 510 (P1) and the pressure of the pressurized fluid in the lumen 544 of the hand piece 549 (P2) are defined by equations (2) and (3) below:

$P1 = F/A1$ $P2 = F/A2,$ where F is the force exerted by the pressurized fluid on the second piston 546, and A1 and A2 are the surface area of the first piston 514 and the second piston 546, respectively. Because the force F acting on the first piston 514 is the same as the force F acting on the second piston 546 under steady-state conditions, equations (2) and (3) can be rearranged to define the relationship between the pressure P2 of the pressurized fluid and the pressure P1 of the dermal filler:

$P1 = (A2/A1) * P2.$

As illustrated by equation (4), the delivery pressure P1 of the dermal filler in the medicament container can be controlled by controlling the pressure P2 of the pressurized fluid in the hand piece 549 and/or by adjusting the area ratio (also referred to as the amplification factor) of the second piston 546 and the first piston 514. In this manner, the hand piece 549 can amplify the pressure of the pressurized fluid.

The hand piece 549 can be configured to produce any desired amount of pressure amplification. For example, in some embodiments, the first piston 514 can have a diameter d1 (i.e., the inner diameter of the medicament container 510) of approximately 5 mm (0.20 inches), and the second piston 546 can have a diameter d2 of approximately 22 mm (0.88 inches). In such embodiments, the amplification factor is approximately 19.3. Accordingly, a pressure within the hand piece 549 of approximately 890 kPa (130 p.s.i.) will result in a pressure within the medicament container of approximately 17.2 MPa (2500 p.s.i.).

In other embodiments, it is desirable for the first piston 514 to have a diameter greater than 5 mm. For example, in some embodiments, the medicament container 510 is configured to contain approximately 2 cubic centimeters of dermal filler, and therefore has an inner diameter of approximately 7 mm (0.28 inches). The second piston 546 can have a diameter d2 of approximately 22 mm (0.88 inches), resulting in an amplification factor of approximately 9.9. Accordingly, a pressure within the hand piece 549 of approximately 690 kPa (100 p.s.i.) will result in a pressure within the medicament container of approximately 6.9 MPa (1000 p.s.i.).

In some embodiments, it is desirable for the second piston 546 to have a diameter less than 22 mm, for example, to provide improved maneuverability during use. For example, in some embodiments, the medicament container 510 is configured to contain approximately 2 cubic centimeters of dermal filler, and has an inner diameter of approximately 7 mm (0.28 inches). The second piston 546 can have a diameter d2 of approximately 15.7 mm (0.62 inches), resulting in an amplification factor of approximately 5. Accordingly, a pressure within the hand piece 549 of approximately 690 kPa (100 p.s.i.) will result in a pressure within the medicament container of approximately 3.5 MPa (500 p.s.i.).

Figure 13:
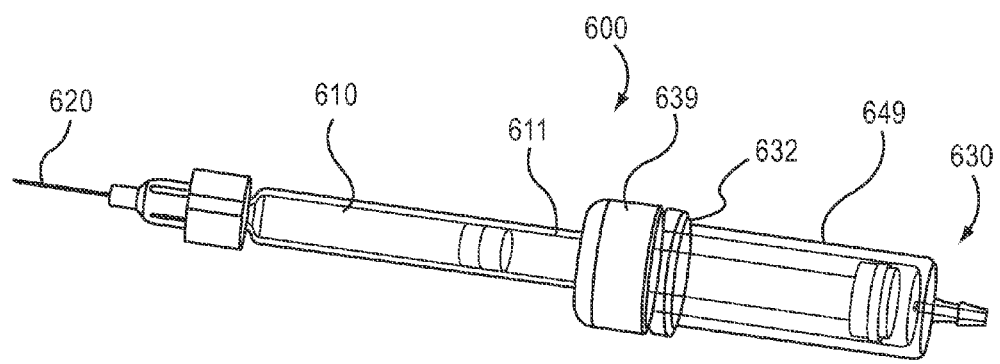
FIG. 13 is a perspective view of a portion of a system for injecting dermal fillers according to an embodiment.

Although the adapter 530 is shown and described above as being coupled to the medicament container 510 by two coupling members 536 configured to engage the flange 513 of the medicament container 510, in other embodiments, an adapter can be coupled to a medicament container in any suitable manner. For example, in some embodiments, an adapter can be coupled to a medicament container by three, four, or more coupling members. In this manner, the medicament container can be securely fastened to the adapter to withstand the high pressures (and therefore the resulting forces) that can be applied during use. In other embodiments, an adapter can be coupled to a medicament container by a nut configured to engage a flange of the medicament container substantially around the entire circumference of the flange. For example, FIG. 13 shows a portion of a system 600 that employs a pressurized fluid to inject a dermal filler according to an embodiment. The system 600 includes a medicament container 610, a needle 620, a source of pressurized fluid (not shown in FIG. 13), and an adapter 630 configured to couple the medicament container 610 to the source of pressurized fluid. The system 600 is similar in many respects to the system 500 described above, and is therefore not described in detail below. The system 600 differs, however, in that the adapter 630 is coupled to the medicament container 610 by a coupling nut 639.

The coupling nut 639 is disposed about the proximal end portion 611 of the medicament container 610 such that a shoulder (not shown) of the coupling nut 639 engages the flange (not shown) of the medicament container 610. The coupling nut 639 is configured to be threadedly coupled to the distal end portion 632 of the hand piece 649. In this manner, when the coupling nut 639 is tightened on to the hand piece 649, the shoulder of the coupling nut 639 exerts a coupling force around the circumference of the flange of the medicament container 610.

Although the regulator 360 is shown and described above as controlling flow rate of dermal filler by regulating the flow rate and/or the pressure of the pressurized fluid delivered from the source of pressurized fluid 351 to the medicament container 310, in other embodiments, a regulator can regulate the flow rate of dermal filler by obstructing and/or modifying a flow path of the dermal filler. Similarly stated, although the regulator 360 is shown and described above as being disposed outside of the flow path of the dermal filler, in other embodiments, a regulator can have at least a portion disposed within the flow path of the dermal filler. For example, FIGS. 14-17 show a system 600 that includes a self-contained source of pressurized gas to inject a dermal filler according to an embodiment.

The system 700 includes a medicament container 710, a needle 720, a source of pressurized fluid 750, and an adapter 730 configured to couple the medicament container 710 to the source of pressurized fluid. The medicament container 710 has a proximal end portion 711 and a distal end portion 712. The medicament container 710 includes a first piston 714 movably disposed therein. The first piston 714 has a diameter d1. The medicament container 710 is configured to contain a dermal filler having a high viscosity. The regulator 760 is disposed at the distal end portion 712 of the medicament container 710. As described in more detail below, a coupler 725 is attached to the regulator and is configured to removably couple the needle 720 to the regulator, and thus to the distal end portion 712 of the medicament container 710. The coupler 725 can be any suitable coupler, as described above. The distal end portion 712 of the medicament container 710 includes a flange 713 that can be coupled to the adapter 730, as described below.

The adapter 730 includes a proximal end portion 731 and a distal end portion 732. The distal end portion 732 of the adapter 730 includes a coupler 733 configured to removably couple the adapter 730 to the medicament container 710. As described above, the coupler 733 includes two coupling members 736 that are disposed approximately equidistance circumferentially about the coupler 733. Said another way, the coupling members 736 are disposed approximately 180 degrees apart. In this manner the coupling members 736 engage the flange 713 of the medicament container 710 at two distinct circumferential locations when the coupler 733 is coupled to the medicament container 710.

Figure 14:
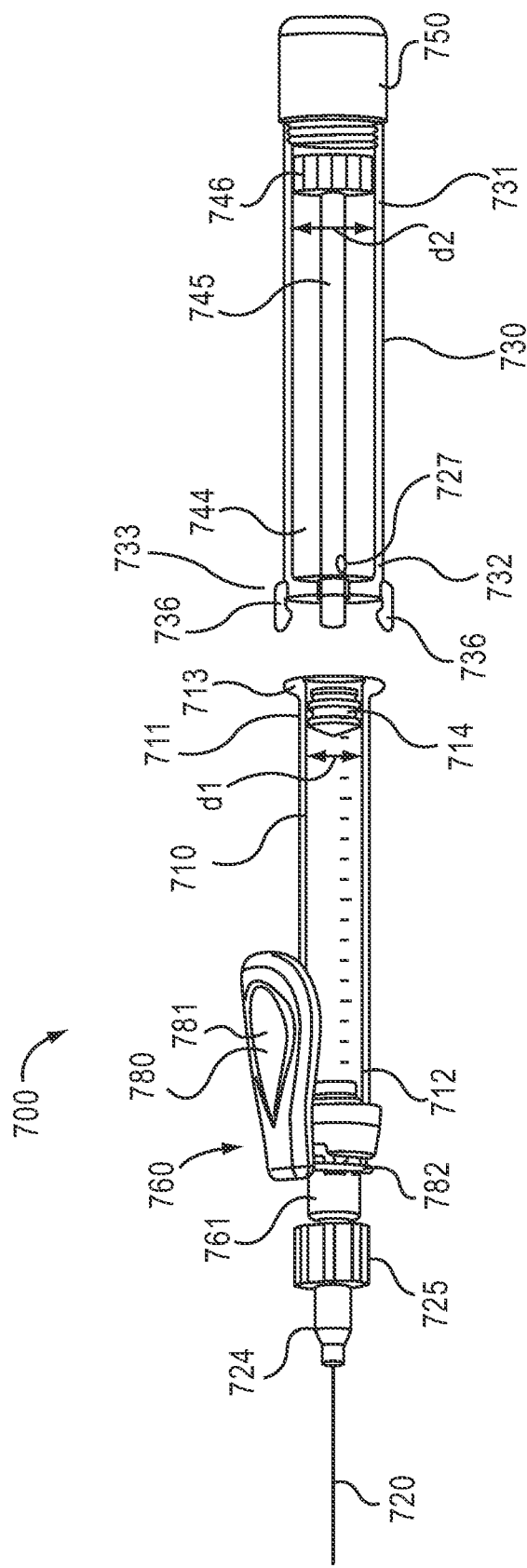
FIG. 14 is a perspective view of a system for injecting dermal fillers including a self-contained source of pressurized fluid according to an embodiment.

The adapter 730 defines a lumen 744, within which a second piston 746, having a diameter d2, and a push rod 745 are movably disposed. When the adapter 730 is coupled to the medicament container 710 by the coupler 733, the second piston 746 is coupled to the first piston 714 by the push rod 745. Accordingly, when the adapter 730 is coupled to the medicament container 710 by the coupler 733, a force acting on the second piston 746 is transferred directly to the first piston 714. In this manner, when a pressurized fluid from the source of pressurized fluid 750 is conveyed into the lumen 744, the force exerted by the pressurized fluid on the second piston 746 is transferred to the first piston 714. As shown in FIG. 14, the diameter d2 of the second piston 746 is greater than the diameter d1 of the first piston 714. In this manner, as described above, the pressure within the medicament container 710 can be greater than the pressure supplied by the source of pressurized fluid 750. Said another way, in this manner, the adapter 730 is configured to amplify the pressure of the pressurized fluid from the source of pressurized fluid 750. In some embodiments, for example, diameter d1 of the first piston 714 can be approximately 7 mm (0.28 inches) and the diameter d2 of the second piston 746 can be approximately 12.7 mm (0.5 inches). With such an arrangement, when the pressure provided by the source of pressurized fluid 750 is approximately 534 kPa (76 p.s.i.), the pressure of the dermal filler within the medicament container 710 is approximately 1.7 MPa (250 p.s.i.).

The outer surface of the adapter 730 defines an opening 727 in fluid communication with the lumen 744. The opening 727 is positioned towards a distal end portion 732 of the adapter 730, and is configured to allow fluid within the lumen 744 distally of the second piston 746 to evacuate from the adapter 730 when the second piston 746 moves distally within the adapter 730. In some embodiments, the opening 727 can include a membrane configured to allow fluids to move through the opening in only one direction. In other embodiments, the opening 727 can be configured to allow fluids to flow freely therethrough in any direction.

The source of pressurized fluid 750 is movably coupled to the proximal end portion 731 of the adapter 730. More particularly, the source of pressurized fluid 750 can be actuated by moving the source of pressurized fluid 750 relative to the adapter 730. In this manner, a valve (not shown in FIG. 14) can be opened thereby releasing pressurized fluid from the source of pressurized fluid 750 into the lumen 744 of the adapter 730. In some embodiments, for example, a release valve (not shown in FIG. 14) can be actuated when the source of pressurized fluid 750 is moved relative to the adapter 730, thereby releasing a pressurized fluid into the lumen 744 of the adapter. The source of pressurized fluid 750 can be any suitable source of pressurized fluid, including those described in U.S. Provisional Application Ser. No. 61/016,223, entitled "Self-Contained Pressurized Injection Device," filed Dec. 21, 2007, which is incorporated herein by reference in its entirety.

Figure 15:
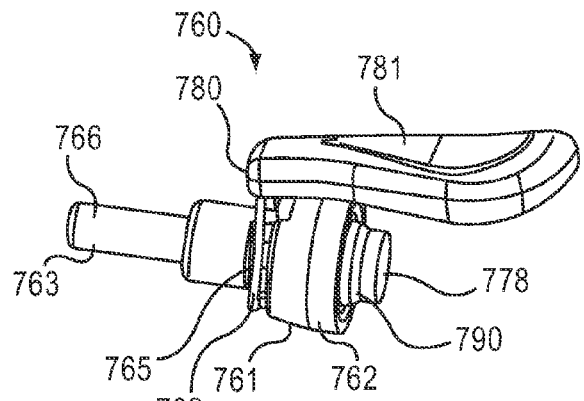
FIG. 15 is a perspective view of a portion of the system for injecting dermal fillers shown in FIG. 14.
Figure 16:
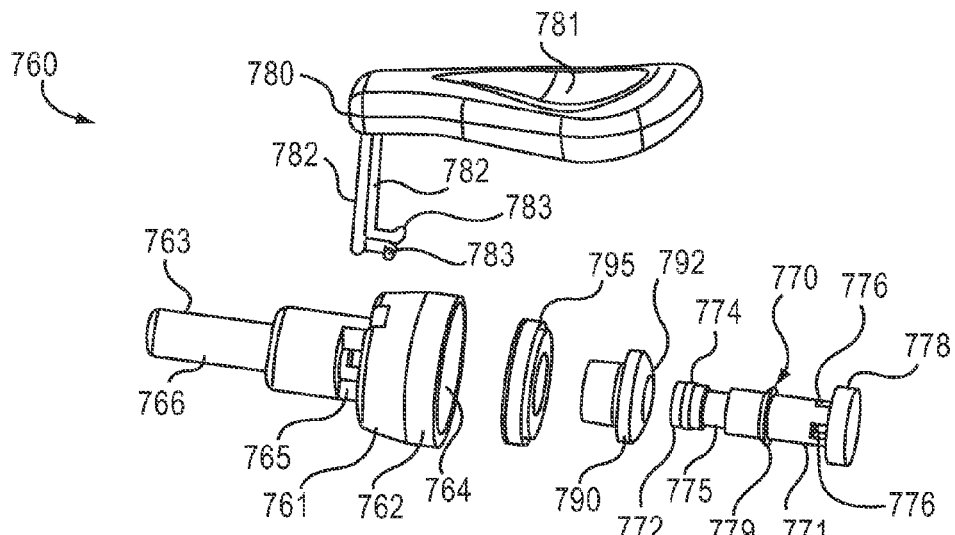
FIG. 16 is an exploded view of the portion of the system for injecting dermal fillers shown in FIG. 15.
Figure 17:
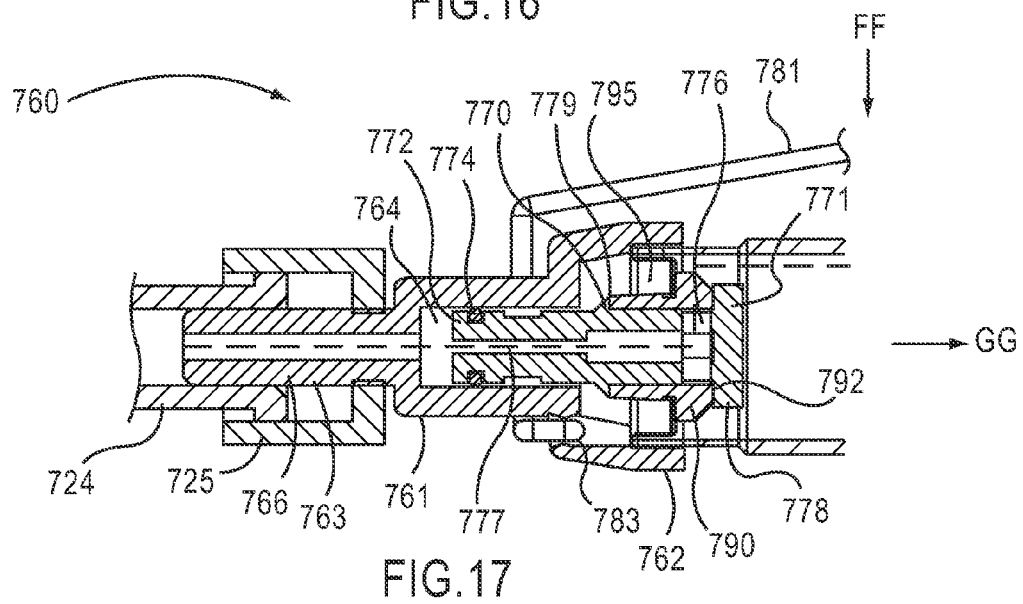
FIG. 17 is a cross-sectional view of the portion of the system for injecting dermal fillers shown in FIG. 15.

As shown in FIGS. 15-17, the regulator 760 includes a regulator body 761, a valve member 770, a valve actuator 780, and a valve seat 790. The valve actuator 780 includes a lever 781 and two elongated members 782. Each of the elongated members 782 includes a protrusion 783, which can be disposed within the regulator body 761 (see e.g., FIG. 17). In this manner, when lever 781 of the valve actuator 780 is moved, the valve actuator 780 can pivot about the protrusions 783.

The regulator body 761 includes a proximal end portion 762 and a distal end portion 763, and defines a lumen 764 therethrough. The side wall of the regulator body 761 defines openings 765 within which a portion of the actuator 780 can be disposed, as described in more detail herein. The distal end portion 763 of the regulator body 761 includes a stem 766, a portion of which is disposed within the hub 724 of the needle 720. As described above, the coupler 725 is attached to the stem 766, and is configured to removably couple the needle 720 to the regulator 760. The proximal end portion 762 of the regulator body 761 is disposed about and coupled to the distal end portion 712 of the medicament container 710. The proximal end portion 762 of the regulator body 761 can be coupled to the distal end portion 712 of the medicament container 710 by any suitable means, such as, for example, an adhesive, a crimped fit, an external clamp or the like.

As shown in FIG. 17, a mounting ring 795 is disposed between the proximal end portion 762 of the regulator body 761 and the distal end portion 712 of the medicament container 710 to provide a substantially fluid-tight seal between the regulator body 761 and the medicament container 710. Moreover, the valve seat 790 is coupled to the mounting ring 795 such that a seat surface 792 is disposed within the medicament container 710 facing in a proximal direction. In this manner, the mounting ring 795 can position the valve seat 790 relative to the regulator body 761 and/or the valve member 770.

The valve member 770 includes a proximal end portion 771 and a distal end portion 772, and defines a lumen 777. The distal end portion 772 of the valve member 770 includes a shoulder 779, a seal 774, and defines an actuation groove 775. As shown in FIG. 17, the seal 774 is configured to engage an inner surface of the regulator body 761 to form a substantially fluid-tight seal between the valve member 770 and the regulator body 761. The actuation groove 775 is configured to receive a portion of each elongated member 782 of the valve actuator 780. In this manner, as described in more detail herein, movement of the actuator 780 can cause the valve member 770 to move longitudinally within the regulator body 761. The proximal end portion 771 of the valve member 770 includes a head 778 and defines openings 776. The openings 776 extend through the side wall of the valve member 770 and are in fluid communication with the lumen 777 of the valve member 770.

The valve member 770 is movably disposed within the lumen 764 of the valve body 761 between a first position (e.g., a closed position, as shown in FIG. 17), a second position (e.g., a fully opened position, not shown in FIGS. 14-17), and any number of positions therebetween. In this manner, the regulator 760 can regulate the flow rate of dermal filler from the medicament container 710 through the needle 720. When the valve member 770 is in the first position, the head 778 of the valve member 770 is disposed against the seat surface 792 of the valve seat 790 to form a substantially fluid-tight seal, as shown in FIG. 17. Accordingly, when the valve member 770 is in the first position, the dermal filler cannot flow from the medicament container 710 through the needle 720. Said another way, when the valve member 770 is in the first position, the flow rate of the dermal filler from the medicament container 710 is substantially zero. Moreover, because the pressure within the medicament container 710 produces a force on the head 778 in a distal direction, the pressure within the medicament container tends to maintain the valve member 770 in the first position. Additionally, as shown in FIG. 17, when the valve member 770 is in the first position, the shoulder 779 of the valve member 770 is disposed against a distal portion of the valve seat 790. In this manner, the valve member 770 is maintained in the first position by the force of the valve seat 790 on the shoulder 779.

To move the valve member 770 from the first position to the second position, the user can move the lever 781 of the valve actuator 780 inward, as shown by the arrow FF in FIG. 17. As described above, the inward movement of the lever 781 causes the valve actuator 780 to pivot about the protrusions 783. In this manner, the elongated members 782 of the valve actuator 780 move proximally. A portion of each of the elongate members 782 is disposed within the actuation groove 775 of the valve member 770. Accordingly, proximal movement of the elongated members 782 causes the valve member 770 to move proximally, as shown by the arrow GG in FIG. 17. The proximal movement of the valve member 770 causes the head 778 to be spaced apart from the seat surface 792, thereby allowing flow of the dermal filler through the openings 776 and into the lumen 777 of the valve member 770. Said another way, the proximal movement of the valve member 770 causes the head 778 to be spaced apart from the seat surface 792, thereby defining a medicament flow path (as shown by the dashed line in FIG. 17).

Moreover, when the valve member 770 is moved proximally, the shoulder 779 exerts a force on the distal portion of the valve seat 790, thereby causing the distal portion of the valve seat 790 to deform. In this manner, the distal portion valve seat 790 acts as a biasing member to urge the valve member 770 towards the first position.

The medicaments and/or dermal fillers described above can be any material suitable for augmenting soft tissue. In some embodiments, a medicament and/or dermal filler can include a pain reliever, such as, for example, lidocaine. In other embodiments, a medicament and/or dermal filler can include a colorant and/or a marker. For example, in some embodiments a medicament and/or dermal filler can include a radio-opaque marker. In other embodiments, a medicament and/or dermal filler can include a tattoo ink.

In some embodiments, a dermal filler can include, for example, a side chain crystalline (SCC) polymer of the type disclosed in International Patent Application No. PCT/US2007/023226, entitled "Compositions, Devices and Methods for Modifying Soft Tissue," which is incorporated herein by reference in its entirety. In other embodiments, a dermal filler can include hyaluronic acid. In yet other embodiments, a dermal filler can include polyacrylamide, collagen (either human and/or bovine), polymethylmethacrylate, silicone, calcium hydroxylapatite (CaHA), hydrophilic polyacrylamid gel (PAAG), and/or poly-L-lactic acid hydrogel (PLLA).

In some embodiments, a dermal filler can include any of the following commercially-available dermal fillers: Puragen™ and its derivatives, produced by Mentor Corporation, Belotero® and its derivatives, produced by Merz Pharmaceuticals, BIO-ALCAMID™ and its derivatives, produced by Polymekon S.R.L., Outline® and its derivatives, produced by ProCytech, HylaNew® and its derivatives, produced by Prollenium Medical Technologies, Inc., Restylane® and its derivatives, produced by Q-Med or Medicis Pharmaceutical Corporation, Reviderm USA and its derivatives, produced by Rofil Medical International N.V., Teosyal® and its derivatives, produced by Teoxane Laboratories, Fascian® and its derivatives, produced by Fascia Biosystems, LLC, FG-5017 and its derivatives, produced by Fibrogen, Inc., Amazingel and its derivatives, produced by FuHua High Molecular Matter Company, Ltd., Laresse® Dermal Filler and its derivatives, produced by FzioMed, Inc., Zyderm® and its derivatives, produced by Inamed Corporation, Isolagen® and its derivatives, produced by Isolagen, Inc., MacDermol® and its derivatives, produced by Laboratories ORGéV, Juvéderm™ and its derivatives, produced by L.E.A. Derm, Hyaluderm® and its derivatives, produced by LCA Pharmaceutical, Silikon® 1000 and its derivatives, produced by Alcon, Inc., Esthélis and its derivatives, produced by Antesis® S.A., Artefill® and its derivatives, produced by Artes Medical, Inc., Radiesse® and its derivatives, produced by BioForm Medical, Inc., Mamidex® and its derivatives, produced by BioPolymer GmbH & Co. KG, Evolence® and its derivatives, produced by ColBar LifeScience Ltd., Aquamid® and its derivatives, produced by Contura International A/S, SurgiDerm® and its derivatives, produced by Labortoire Corneal® Development, Rhegecoll and its derivatives, produced by Dermabiol Institute of Kuhra Vital GmbH, DermaLive® and its derivatives, produced by Derma Tech, and/or Sculptra™ and its derivatives, produced by Dermik® Laboratories.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the energy sources are shown and described above as including a pressurized fluid, in other embodiments, an energy source can include any suitable form of stored energy and/or a mechanism configured to convert energy from one form to another. For example, in some embodiments an energy source can include a source of stored electrical energy (e.g., a battery), a source of chemical energy (e.g., products that react to produce energy), and/or a source of mechanical energy (e.g., a spring). In other embodiments, an energy source can include a mechanism configured to convert electrical potential energy to a kinetic energy. For example, in some embodiments, an energy source can include an electric motor (e.g., a stepper motor) configured to receive electrical energy (from a battery or from an AC power source) and convert the electrical energy into a kinetic energy to move a piston.

Although the medicament containers are shown and described above as including a piston, in other embodiments, a medicament container can be devoid of a piston. For example, in some embodiments, a fluid powered injection system can include a medicament container devoid of a piston, and include a source of pressurized fluid. The dermal filler contained within the medicament container can have a high viscosity such that it will not readily mix with the pressurized fluid. Accordingly, to actuate the injector, the pressurized fluid is conveyed into the medicament container and in direct contact with the dermal filler to be injected, thereby moving the dermal filler within the medicament container.

Although the coupling members 436 are shown and described as being configured to bend outwardly when the coupler 433 is being coupled to the medicament container 410, in other embodiments, the coupling members 436 can be substantially rigid. For example, in some embodiments, the flange 413 of the medicament container 410 does not extend circumferentially around the medicament container 410, but rather there may be two flanges positioned on opposite sides of the medicament container 410. In such embodiments, the medicament container 410 can be rotated relative to the hand piece 449 until the flanges are out of alignment with the coupling members 436. The hand piece 449 can then be disposed about the medicament container 410. The medicament container 410 can then be rotated relative to the hand piece 449 until the flanges are aligned with the coupling members 436, thereby securing the medicament container within the hand piece 449.

In some embodiments, for example, an apparatus includes a medicament container, a needle, an energy source, and a regulator. The medicament container has a piston movably disposed therein such that the medicament container is divided into a first portion and a second portion. The first portion of the medicament container is configured to contain a medicament, such as, for example a dermal filler. The needle is coupled to the medicament container such that the needle is in fluid communication with the first portion of the medicament container. The energy source is operatively coupled to the piston and is configured to produce a kinetic energy to move the piston within the medicament container such that the medicament having a viscosity of at least 1000 Poise (100 N-sec/m$^2$) can be conveyed from the first portion of the medicament container through a distal end of the needle at a flow rate of at least 0.02 cubic centimeters per minute. The regulator is configured to regulate the flow rate of the medicament through the distal end of the needle.

In some embodiments, for example, an apparatus includes a medical injector, a pressurized fluid source, and a regulator. The medical injector is configured to contain a dermal filler, and includes a needle. The needle defines a lumen therethrough having a nominal inner diameter of less than approximately 0.140 millimeters (i.e., the needle is smaller than 30 gauge), and has a length of at least 17 millimeters. The pressurized fluid source, which can include, for example, a canister of pressurized fluid, is operatively coupled to the medical injector. A pressurized fluid from the pressurized fluid source has a pressure of at least 345 kilopascals. The pressurized fluid is configured to actuate the medical injector such that the dermal filler can be conveyed from the medical injector through the lumen of the needle. The regulator is configured to regulate the flow rate of the dermal filler through the lumen of the needle.

Although various embodiments have been described as having particular features and/or combinations of components, other embodiments are possible having a combination of any features and/or components from any of embodiments where appropriate. For example, in some embodiments, a medical device can include a remotely located source of pressurized fluid, such as the source of pressurized fluid 351 shown and described above, and a regulator coupled to the medicament container, such as the regulator 760 shown and described above.

What is claimed is:

1. A method, comprising
receiving a syringe pre-filled by a dermal filler supplier such that a first portion of the syringe contains a dermal filler, the syringe having a piston movably disposed therein such that the syringe is divided into the first portion and a second portion, the first portion of the syringe being coupled to a needle;
coupling the second portion of the syringe to a non-manual energy source via a hand piece such that the first portion of the syringe is unconstrained by the hand piece, the coupling including disposing a push rod of the hand piece within the second portion of the syringe such that the push rod is adjacent the piston of the syringe;
inserting a distal end portion of a needle into a skin of a body;
actuating the non-manual energy source such that a gas having a first pressure is supplied to the hand piece, the hand piece configured to amplify the first pressure such that the dermal filler is conveyed from the first portion of the syringe at a second pressure higher than the first pressure, the dermal filler conveyed into the skin through the distal end portion of the needle; and
moving the distal end portion of the needle within the skin during the actuating.

2. The method of claim 1, wherein the inserting includes inserting the distal end portion of the needle into a subcutaneous tissue of the skin.

3. The method of claim 1, wherein:
the non-manual energy source includes a pressurized fluid; and
the actuating includes conveying the pressurized fluid to the hand piece such that the dermal filler is conveyed from the first portion of the syringe through the distal end portion of the needle.

4. The method of claim 1, further comprising:
regulating a flow rate of the dermal filler through the distal end portion of the needle during the actuating.

5. The method of claim 1, further comprising:
moving a valve body within a medicament flow path defined within the syringe such that a flow rate of the dermal filler through the distal end portion of the needle is regulated.

6. The method of claim 1, further comprising:
regulating the non-manual energy source such that a flow rate of the dermal filler through the distal end portion of the needle is at least 0.02 cubic centimeters per minute.

7. The method of claim 1, further comprising:
regulating a flow rate of the dermal filler through the distal end portion of the needle at a first time after the moving, without removing the needle from the skin between the inserting and the regulating, such that the flow rate of the dermal filler is substantially zero;
moving the distal end portion of the needle within the skin when the flow rate of the dermal filler is substantially zero; and
regulating a flow rate of the dermal filler through the distal end portion of the needle at a second time after the first time, without removing the needle from the skin between the regulating at the first time and the regulating at the second time such that the flow rate of the dermal filler is greater than zero.

8. The method of claim 1, wherein:
the inserting includes inserting the distal end portion of the needle into the skin in a distal direction; and
the moving includes moving the distal end portion of the needle in a proximal direction.

9. The method of claim 1, wherein:
the moving includes moving the needle from a first location within the skin to a second location within the skin, the first location spaced apart from the second location by at least 4 millimeters.

10. The method of claim 1, wherein the skin is any one of facial skin or skin of a neck region of the body.

11. The method of claim 1, wherein the syringe is a rigid syringe.

12. The method of claim 1, wherein the coupling includes disposing a flange of the syringe within a coupling portion of the hand piece such that the first portion of the syringe is visible to a user.

13. The method of claim 1, wherein the inserting includes inserting the needle at an angle relative to a surface of the skin of not greater than between approximately 5 degrees and approximately 35 degrees.

14. The method of claim 1, wherein the hand piece is configured to amplify the first pressure such that the second pressure is greater than 100 pounds per square inch.

15. The method of claim 1, wherein the hand piece is configured to amplify the first pressure such that the second pressure is greater than 150 pounds per square inch.

16. The method of claim 1, wherein the hand piece is configured to amplify the first pressure such that the second pressure is approximately 250 pounds per square inch.

17. A method, comprising:
coupling a proximal end portion of a syringe to a non-manually-powered machine using a hand piece such that a distal end portion of the syringe and a central portion of the syringe are unconstrained, at least the distal end portion configured to contain a dermal filler, the distal end portion coupled to a needle;
inserting a distal end portion of a needle into a skin of a body; and
actuating the non-manually-powered machine operatively coupled to the hand piece such that a gas having a first pressure is supplied to the hand piece, the hand piece configured to amplify the first pressure such that the dermal filler is conveyed from the distal portion of the syringe at a second pressure higher than the first pressure into the skin through the distal end portion of the needle, the second pressure being approximately 250 pounds per square inch.

18. The method of claim 17, further comprising:
regulating a flow rate of the dermal filler through the distal end portion of the needle during the actuating.

19. The method of claim 17, further comprising:
moving a valve body within a medicament flow path such that a flow rate of the dermal filler through the distal end portion of the needle is regulated.

20. The method of claim 17, wherein:
the inserting includes inserting the distal end portion of the needle into the skin in a distal direction; and
the moving includes moving the distal end portion of the needle in a proximal direction.

21. The method of claim 17, wherein the skin is any one of facial skin or skin of a neck region of the body.

22. The method of claim 17, wherein
the actuating includes actuating the non-manually-powered machine such that at least 0.5 cubic centimeters of the dermal filler is conveyed into the skin through the distal end portion of the needle.

23. The method of claim 17, further comprising:
moving the distal end portion of the needle within the skin during the actuating.

24. The method of claim 17, wherein the coupling includes disposing a flange of the syringe within a coupling portion of the hand piece such that the distal end portion of the syringe and the central portion of the syringe are unobstructed by the hand piece.

25. The method of claim 17, wherein the coupling is performed such that the distal end portion of the syringe can be manipulated by a user.

26. The method of claim 17, wherein the inserting includes inserting the needle at an angle relative to a surface of the skin not greater than between approximately 5 degrees and approximately 35 degrees.

27. The method of claim 17, wherein the inserting includes inserting the needle at an angle relative to a surface of the skin of approximately 20 degrees.

28. The method of claim 17, wherein:
the dermal filler has a viscosity of at least 1000 centipoise; and
the hand piece is configured to amplify the first pressure such that the dermal filler is conveyed from the first portion of the syringe at a flow rate of at least 0.02 cubic centimeters per minute.

29. The method of claim 17, wherein:
the syringe has a piston movably disposed therein; and
the coupling includes disposing a push rod of the hand piece within the proximal end portion of the syringe such that the push rod is in contact with the piston of the syringe.

30. A method, comprising:
coupling a proximal end portion of a syringe to a hand piece such that a push rod of the hand piece is disposed adjacent a piston within the syringe and such that the syringe and the hand piece collectively define a range of minimum insertion angles relative to a surface of a skin of a body between approximately 5 degrees and approximately 35 degrees;
inserting a distal end portion of a needle coupled to the syringe into the skin of the body at an angle relative to the surface of the skin; and
actuating a pneumatic energy source operatively coupled to the syringe via the hand piece such that the hand piece receives a gas having a gas pressure from the pneumatic energy source, and amplifying the gas pressure via the hand piece such that a pressure of the dermal filler within the syringe is higher than the gas pressure and is approximately 250 pounds per square inch, such that a dermal filler is conveyed from the syringe into the skin through the distal end portion of the needle.

31. The method of claim 30, wherein:
the dermal filler has a viscosity of at least 1000 centipoise; and
the amplifying includes amplifying the first pressure such that the dermal filler is conveyed from the first portion of the syringe at a flow rate of at least 0.02 cubic centimeters per minute.

32. The method of claim 30, comprising:
moving the distal end portion of the needle within the skin during the actuating.

33. The method of claim 30, wherein:
the coupling includes coupling a flange of the syringe to the hand piece such that at least a central portion of the syringe and a distal end portion of the syringe are exposed.

\* \* \* \* \*

UNITED STATES PATENT AND TRADEMARK OFFICE
CERTIFICATE OF CORRECTION

PATENT NO. : 8,343,132 B2
APPLICATION NO. : 12/871405
DATED : January 1, 2013
INVENTOR(S) : Scott Heneveld et al.

It is certified that error appears in the above-identified patent and that said Letters Patent is hereby corrected as shown below:

Title Page at (60), line 7, change "74" to --2007--.

Signed and Sealed this
Second Day of April, 2013

Teresa Stanek Rea
*Acting Director of the United States Patent and Trademark Office*